US010067088B2

(12) United States Patent
Henry et al.

(10) Patent No.: US 10,067,088 B2
(45) Date of Patent: Sep. 4, 2018

(54) GRADIENT ELUTION ISOTACHOPHORETIC APPARATUS FOR SEPARATING, PURIFYING, CONCENTRATING, QUANTIFYING, AND/OR EXTRACTING CHARGED ANALYTES AND METHODS THEREOF

(71) Applicants: Alyssa Henry, Arlington, VA (US); Christopher Konek, Alexandria, VA (US); David Ross, Bethesda, MD (US); Elizabeth Strychalski, North Potomac, MD (US)

(72) Inventors: Alyssa Henry, Arlington, VA (US); Christopher Konek, Alexandria, VA (US); David Ross, Bethesda, MD (US); Elizabeth Strychalski, North Potomac, MD (US)

(73) Assignees: Applied Research Associates, Inc., Albuquerque, NM (US); The United States of America, as Represented by the Secretary of Commerce National Institute of Standards and Technology, Washington, DC (US)

( * ) Notice: Subject to any disclaimer, the term of this patent is extended or adjusted under 35 U.S.C. 154(b) by 406 days.

(21) Appl. No.: 14/746,269

(22) Filed: Jun. 22, 2015

(65) Prior Publication Data
US 2016/0139078 A1 May 19, 2016

Related U.S. Application Data

(60) Provisional application No. 62/015,153, filed on Jun. 20, 2014.

(51) Int. Cl.
*G01N 27/453* (2006.01)
*G01N 27/447* (2006.01)
*C12N 15/10* (2006.01)

(52) U.S. Cl.
CPC ..... *G01N 27/44765* (2013.01); *C12N 15/101* (2013.01); *G01N 27/4473* (2013.01); *G01N 27/44721* (2013.01); *G01N 27/44743* (2013.01)

(58) Field of Classification Search
CPC .......... G01N 27/447; G01N 27/44704; G01N 27/44721; G01N 27/4473; G01N 27/44765; G01N 27/453
See application file for complete search history.

(56) References Cited

U.S. PATENT DOCUMENTS 3,893,813 A * 7/1975 Johnson .................... B01L 9/50
24/504
5,098,826 A 3/1992 Wilkins et al.
(Continued)

OTHER PUBLICATIONS

Product description of the Villa Labeco Electrophoretic Analyser EA 102, publication date unknown, downloaded http://www.villalabeco.sk/eng_ponuka_EA102.htm (Year: 2017).*

(Continued)

*Primary Examiner* — Alexander S Noguerola
(74) *Attorney, Agent, or Firm* — Dinsmore & Shohl LLP

(57) ABSTRACT

Gradient elution isotachophoretic apparatus, and systems for performing gradient elution isotachophoresis to separate, purify, concentrate, quantify, and/or extract charged analytes from a sample. The isotachophoretic apparatus include an electrophoretic assembly, a sampling assembly connected to the electrophoretic assembly, and/or a support structure connected to the electrophoretic assembly and/or to the sampling assembly. The system includes an isotachophoretic apparatus, and a controller communicatively coupled to the isotachophoretic apparatus. The controller includes a storage medium and a processor for executing computer readable and executable instructions.

19 Claims, 25 Drawing Sheets

(56) References Cited

U.S. PATENT DOCUMENTS

| | | | |
|---|---|---|---|
| 5,482,608 | A | 1/1996 | Keely et al. |
| 5,757,014 | A * | 5/1998 | Bruno .................. G01N 21/645 |
| | | | 250/458.1 |
| 5,958,202 | A | 9/1999 | Regnier et al. |
| 6,110,696 | A | 8/2000 | Brown et al. |
| 7,029,561 | B2 | 4/2006 | Ross et al. |
| 7,537,680 | B2 | 5/2009 | Ross et al. |
| 7,572,357 | B2 | 8/2009 | Ross et al. |
| 8,080,144 | B2 | 12/2011 | Ross et al. |
| 2004/0206626 | A1 | 10/2004 | Ross et al. |
| 2010/0155241 | A1 * | 6/2010 | Ross ..................... B01D 57/02 |
| | | | 204/451 |

OTHER PUBLICATIONS

Poster by Špalková et al. entitled "Utilization of Isotachophoresis for Control of Anaerobic Digestion", publication date unknown, downloaded from http://kchbi.chtf.stuba.sk/cevoze/doc/pod9/poster/Utilization%20of%20isotachophoresis%20for%20control%20of%20anaerobic%20digestion.pdf (Year: 2017).*

Praus et al., "A Physico-Chemical Study of the Cationic Surfactants Adsorption on Montmorillonite," J. Braz. Chem. Soc. vol. 18, No. 2 378-383, 2007 (Year: 2017).*

Novotný et al., "Improved dual photometric-contactless conductometric detector for capillary electrophoresis," Analytica Chimica Acta 525 (2004) 17-21 (Year: 2004).*

Breadmore, et al., Determination of ribavirin in human serum and plasma by capillary electrophoresis, Electrophoresis, 2004, vol. 25, pp. 1615-1622, Switzerland.

Dittrich, et al., Micro Total Analysis Systems. Latest Advancements and Trends, Anal Chem, vol. 78, pp. 3887-3907 (2006), USA.

Heiger, et al., Determination of Small Ions by Capillary Zone Electrophoresis with Indirect Photometric Detection, Environmental and Food Analysis, Application Note, Agilent Technologies, 1994, pp. 1-16.

Suarez-Luque, et al., Determination of major metal cations in milk by capillary zone electrophoresis, International Dairy Journal, vol. 17, Issue 8, pp. 896-901, Aug. 2007, USA.

Savitzky et al., Smoothing and Differentiation of Data by Simplified Least Squares Procedures, Anal Chem, vol. 36, Issue 8, pp. 1627-1639, Jul. 1964, USA.

Shackman et al., "Electrophoretic Separations in Small Spaces: Gradient Elution Moving-Boundary Electrophoresis (GEMBE)", The 10th International Conference on Miniaturized Systems for Chemistry and Life Sciences, Nov. 5-9, 2006, pp. 912-914, Tokyo, Japan.

Strawbridge, et al., Measurement of Particle Size Distributions in Milk Homogenized by a Microfluidizer: Estimation of Populations of Particlees with Radii Less Than 100 nm, Journal of Colloid and Interface Science, vol. 171, Issue 2, May 1995, pp. 392-398, Canada.

Strychalski, et al., Microfluidic Analysis of Complex Samples with Minimal Sample Preparation Using Gradient Elution Moving Boundary Electrophoresis, Anal. Chem., vol. 81, No. 24, pp. 10201-10207, 2009, USA.

Strychalski, et al., DNA purification from crude samples for human identification using gradient elution isotachophoresis, Electrophoresis Journal,vol. 34, pp. 2522-2530, 2013, Switzerland.

Tiselius, "A New Apparatus for Electrophoretic Analysis of Colloidal Mixtures", Trans Faraday Soc, vol. 33, pp. 524-531, Jan. 25, 1937.

Vrouwe, et al., Microchip analysis of lithium in blood using moving boundary electrophoresis and zone electrophoresis, Electrophoresis Journal, vol. 26, pp. 3032-3042, 2005, Switzerland.

* cited by examiner

GRADIENT ELUTION ISOTACHOPHORETIC APPARATUS FOR SEPARATING, PURIFYING, CONCENTRATING, QUANTIFYING, AND/OR EXTRACTING CHARGED ANALYTES AND METHODS THEREOF

CROSS-REFERENCE TO RELATED APPLICATIONS

This application claims the benefit under 35 U.S.C. § 119 of U.S. Provisional Patent Application No. 62/015,153, filed on Jun. 20, 2014, entitled, "Gradient Elution Isotachophoretic Apparatus for Separating, Purifying, Concentrating, Quantifying, and/or Extracting Charged Analytes and Methods Thereof", the contents of which are hereby incorporated by reference in their entirety.

STATEMENT OF GOVERNMENT RIGHTS

This invention was made with government support from the United States Army Research Laboratory under the Government Contract No. W911QX-11-C-0089. The United States Government may have certain rights in this invention.

TECHNICAL FIELD

The present disclosure generally rates to electrophoretic apparatus, and more particularly, relates to gradient elution isotachophoretic apparatus for separating, purifying, concentrating, quantifying, and/or extracting charged analytes, to systems for performing gradient elution isotachophoresis, and to methods for separating, purifying, concentrating, quantifying, and/or extracting charged analytes from samples.

BACKGROUND

The separation, purification, concentration, quantification, and/or extraction of charged analytes, such as, e.g., biomolecules and/or deoxyribonucleic acid (i.e., DNA), from crude samples remains a technical and practical challenge. For example, crude samples may contain environmental contaminants, such as, e.g., soil, blood, bacteria, particulate material, cell detritus, and/or ionic species, and/or biomolecule inhibitors, such as, e.g., qPCR inhibitors such as polymerase inhibitors, which complicate analysis thereof. Additionally, conventional apparatus and/or techniques for analyzing crude samples are generally labor intensive, time consuming, and/or require access to a laboratory, skilled technicians, and/or specialized equipment. Moreover, such apparatus and/or techniques typically deliver the purified analytes, such as, e.g., DNA, in small fluid volumes, such as, e.g., about 50 μL, which limits further analysis thereof. Further, conventional apparatus and/or methods for separation of charged analytes from crude samples may require pre-separation and/or post-separation sample preparation steps, such as, e.g., filtration, centrifugation, and/or precipitation. Such further sample preparation steps may reduce the quantity of charged analytes delivered from the sample and may also lower the final concentration of charged analytes. The reduction of both quantity and concentration of delivered charged analytes can negatively impact the likelihood of further post-separation analyses, such as, e.g., in the case of DNA, short tandem repeat (i.e., STR) analysis for human identification. Accordingly, additional embodiments of apparatus for separating, purifying, concentrating, quantifying, and/or extracting charged analytes and methods thereof are desired.

SUMMARY OF THE INVENTION

In one embodiment, an apparatus for performing gradient elution isotachophoresis (GEITP) to separate charged analytes in a sample is disclosed. The apparatus may include a moveable electrophoretic assembly including: a separation unit, a detection unit operably connected to the separation unit, wherein the detection unit includes: a support structure, a conductivity detection device accommodated by the support structure, a light source accommodated by the support structure, and a light source detection device accommodated by the support structure, and at least one moveable support structure connected to at least one of the separation unit or the detection unit; a sampling assembly operably connected to the moveable electrophoretic assembly; and a support structure connected to at least one of the moveable electrophoretic assembly or the sampling assembly.

In another embodiment, a system for performing gradient elution isotachophoresis (GEITP) to separate charged analytes in a sample is disclosed. The system includes: an apparatus for performing GEITP including: a moveable electrophoretic assembly including: a separation unit including at least one separation channel in a vertical orientation, a leading electrolyte (LE) reservoir in open fluidic communication with the at least one separation channel, a voltage supply device communicatively coupled to the at least one separation channel, and a pressure control device connected to the LE reservoir, a detection unit operably connected to the separation unit, wherein the detection unit includes a support structure, a conductivity detection device accommodated by the support structure, a light source accommodated by the support structure, and a light source detection device accommodated by the support structure, at least one moveable support structure connected to at least one of the separation unit or the detection unit; a sampling assembly operably connected to the moveable electrophoretic assembly, wherein the sampling assembly includes a trailing electrolyte (TE) reservoir and a delivery reservoir, wherein the TE reservoir includes the sample and TE fluid; a support structure connected to at least one of the moveable electrophoretic assembly or the sampling assembly; and a controller communicatively coupled to the moveable electrophoretic assembly and the sampling assembly, wherein the controller includes a storage medium including computer readable and executable instructions and a processor for executing the computer readable and executable instructions, wherein the processor executes the computer readable and executable instructions to: (1) optionally pre-treat the at least one separation channel, (2) insert LE fluid and sensor molecules from the LE reservoir into the at least one separation channel, (3) contact the at least one separation channel with the sample and TE fluid in the TE reservoir of the sampling assembly, (4) separate the charged analytes via GEITP by: (a) producing a pressure-driven counterflow of the LE fluid through the at least one separation channel with the pressure control device and/or the voltage supply device, (b) applying a voltage to the at least one separation channel with the voltage supply device to produce an electric field, thereby driving electrophoretic migration of charged analytes in the TE reservoir of the sampling assembly toward the at least one separation channel, and (c) varying with respect to time the pressure-driven counterflow through the at least one separation channel with the pressure control device to control focusing of the charged analytes via initiation of a pressure ramp, thereby focusing and separating the charged analytes, (5) direct light through the at least one separation channel to excite fluorescence in any of the charged analytes contacted with the sensor molecules, (6) detect the charged analytes in the at least one separation channel via conductivity detection with the conductivity detection device and/or fluorescence detection with the light source detection device, and (7) deliver the charged analytes to a delivery reservoir in the sampling assembly.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

Figure 1:
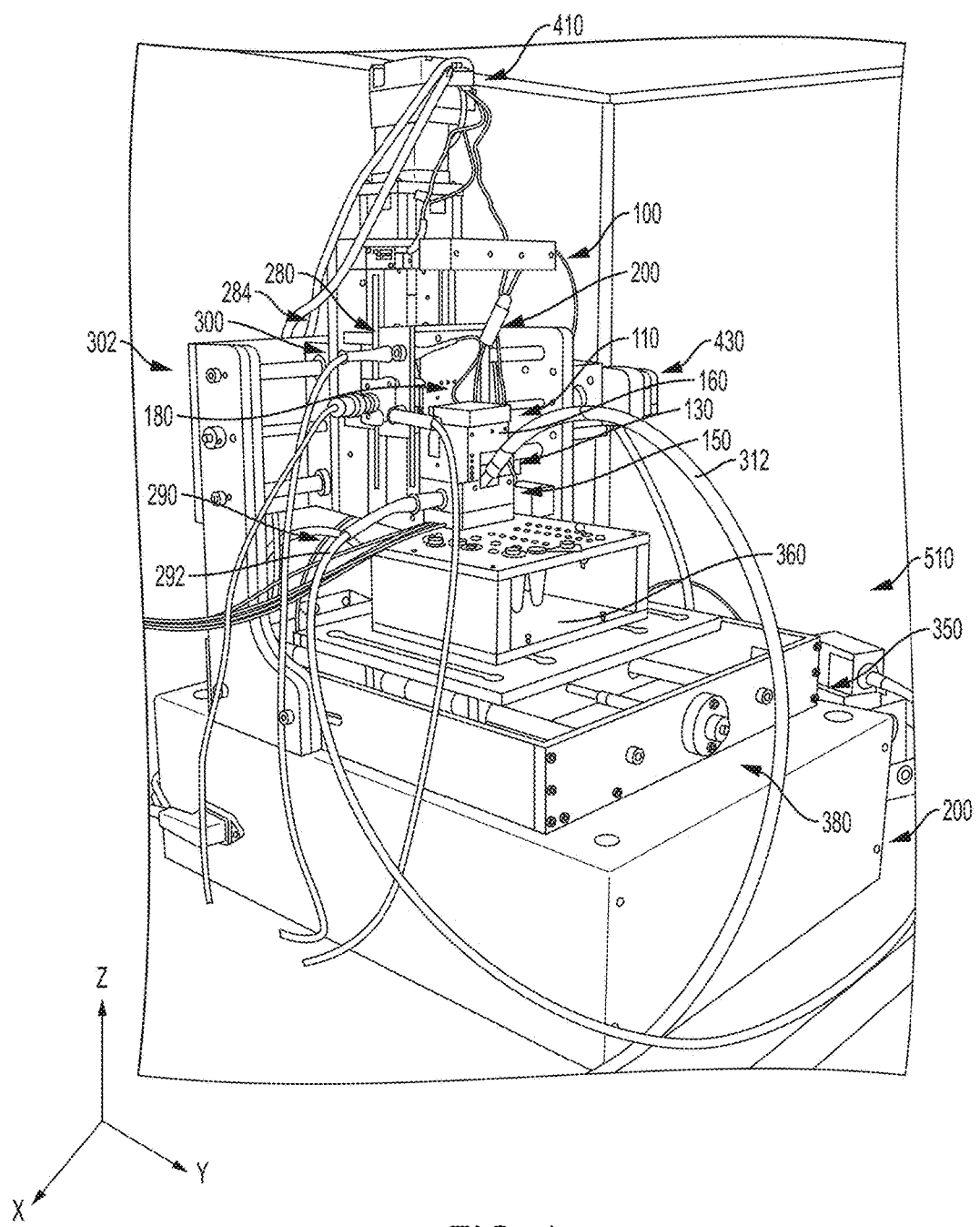
FIG. 1 is a side perspective view of a gradient elution isotachophoretic apparatus according to embodiments described herein.

Skilled artisans appreciate that elements in the figures are illustrated for simplicity and clarity and are not necessarily drawn to scale. For example, the dimensions of some of the elements in the figures may be exaggerated relative to other elements, as well as conventional parts removed, to help to improve understanding of the various embodiments of the present disclosure.

DETAILED DESCRIPTION OF THE INVENTION

The following terms are used in the present application:

As used herein, the term "communicatively coupled" refers to the electrical, signal, wireless, wired, and/or optical interconnectivity of various components of the gradient elution isotachophoretic apparatus which are connected, such as, e.g., through wires, through optical fibers, and/or wirelessly, such that electrical, optical, and/or electromagnetic signals may be exchanged therebetween.

As used herein, the term "crude sample" refers to a specimen suspected of containing charged analytes of interest, such as, e.g., positively charged analytes and/or negatively charged analytes, and/or particulates, which has not undergone procedures for the separation, concentration, purification, and/or extraction thereof. In further embodiments, the crude sample refers to a specimen which has also not undergone sample preparation procedures, including but not limited to pre-separation and/or post-separation sample preparation procedures, such as, e.g., filtration, centrifugation, and/or precipitation (excluding simple dilution and lysis in some embodiments). In particular embodiments, crude sample refers to a specimen suspected of containing negatively charged small inorganic species, such as, e.g., chloride, bromide iodide, chlorate, perchlorate, iodate, and/or periodate, which has not undergone procedures for the separation, concentration, purification, and/or extraction thereof. In other particular embodiments, crude sample refers to a specimen suspected of containing negatively charged organic species, such as, e.g., acetate, formate, lactate, and/or biomolecules such as, e.g., DNA and/or RNA, which has not undergone procedures for the separation, concentration, purification, and/or extraction thereof. Where the charged analytes of interest include biomolecules, such as, e.g., DNA and/or RNA, cells in the crude sample may be lysed. Additionally, where the charged analytes of interest include biomolecules, by way of example, a buccal swab and/or a soiled buccal swab of cheek cells may be a crude sample. In still other particular embodiments, crude sample refers to a specimen suspected of containing positively charged species, such as, e.g., copper, which has not undergone procedures for the separation, concentration, purification, and/or extraction thereof. For example, crude samples may contain environmental contaminants, such as, e.g., soil, blood, bacteria, particulates, cell detritus, solid cell lystae, plant material detritus, and/or ionic species, and/or biomolecule inhibitors, such as, e.g., qPCR inhibitors such as polymerase inhibitors.

As used herein, the term "gradient elution isotachophoresis" refers to a fluid-phase electroseparation technique that involves concentration of charged analytes via isotachophoresis (i.e., ITP) and controlled focusing of such charged analytes via pressure-driven counterflow. In some embodiments, the pressure-driven counterflow improves control and/or selectivity of the charged analytes during focusing thereof and/or excludes contaminants from focusing with the charged analytes. In further embodiments, the pressure-driven counterflow excludes contaminants, such as, e.g., particulates, inhibitors, and/or other contaminant molecules, from being introduced into a separation channel in which the gradient elution isotachophoresis (i.e., GEITP) occurs. GEITP is further described in U.S. Pat. No. 8,080,144, the contents of which are hereby incorporated by reference in their entirety, As used herein, the term "isotachophoresis" refers to the separation and/or concentration of charged analytes in a sample which is introduced in between a zone of leading electrolyte (i.e., LE) fluid, such as, e.g., LE solution, and a zone of trailing electrolyte (i.e., TE) fluid, such as, e.g., TE solution, upon application of an electric field thereto. The LE fluid includes electrophoretically fast ions and the TE fluid includes electrophoretically slow ions (relative to the electrophoretic mobility of the charged analytes). The charged analytes have an electrophoretic mobility which is intermediate to the electrophoretically fast ions of the LE fluid and the electrophoretically slow ions of the TE fluid. Upon application of the electric field, the charged analytes focus at the interface of the LE fluid and the TE fluid.

As used herein, the term "selective fluidic communication" refers to the controlled flow and/or lack of flow of a fluid from a first position to a second position. When a fluid flows and/or is capable of flowing from a first position to a second position, the fluidic communication is open therebetween. When a fluid does not flow and/or is incapable of flowing from a first position to a second position, the fluidic communication is closed therebetween.

Embodiments of the present disclosure are directed toward gradient elution isotachophoretic apparatus for performing GEITP. More specifically, embodiments of the present disclosure are directed toward gradient elution isotachophoretic apparatus for separating, purifying, concentrating, quantifying, and/or extracting charged analytes (hereinafter, "isotachophoretic apparatus") in and/or from a sample via GEITP. In further embodiments, the present disclosure is directed toward isotachophoretic apparatus for performing automated GEITP.

Embodiments of the isotachophoretic apparatus will now be described in detail with reference to FIGS. 1-16. Thereafter, embodiments of isotachophoretic systems will be described with reference to FIG. 23. Finally, methods for separating, purifying, concentrating, quantifying, and/or extracting charged analytes will be described with reference to FIG. 17.

I. Isotachophoretic Apparatus

Referencing FIGS. 1-4, in one or more embodiments, an isotachophoretic apparatus 100 includes an electrophoretic assembly 110, a sampling assembly 350 operably connected to the electrophoretic assembly 110, and/or a support structure 510 connected to the electrophoretic assembly 110 and/or to the sampling assembly 350.

Referring to FIGS. 1-5, in one or more embodiments, the isotachophoretic apparatus 100 includes an electrophoretic assembly 110. In some embodiments, the electrophoretic assembly 110 is moveable. In embodiments, the electrophoretic assembly 110 includes a separation unit 130, a detection unit 230 operably connected and/or communicatively coupled to the separation unit 130, and a first and second moveable support structure 280, 300 attached to, connected to, and/or attachable to the separation unit 130 and/or to the detection unit 230. In one or more embodiments, the separation unit 130 includes at least one separation channel 140, a leading electrolyte (i.e., run buffer) reservoir 160 in fluidic communication with the at least one separation channel 140, a voltage supply device 180 electrically connected and/or communicatively coupled to the separation channel 140, and/or a pressure control device 200 connected to the leading electrolyte reservoir 160.

Referring to FIGS. 5-8, in one or more embodiments, the separation unit 130 includes at least one separation channel 140. In some embodiments, the separation channel 140 includes an elongate body which defines a channel (not shown) therethrough. In some embodiments, the channel (not shown) extends from an inlet 144 to an outlet (not shown). In further embodiments, the channel (not shown) extends from the inlet 144 to the outlet, along a length L of the elongate body. In still further embodiments, the elongate body includes a length L of from about 5 cm to about 100 cm, or from about 6 cm to about 50 cm, or from about 7 cm to about 20 cm, or about 10 cm. In one particular embodiment, the elongate body includes a length L of about 8.4 cm.

In embodiments, the elongate body has a substantially circular, ovular, oblong, and/or square cross-sectional shape. In some embodiments, the body has an inner diameter (not shown) of from about 1 µm to about 200 µm, or from about 5 µm to about 150 µm, or from about 15 µm to about 100 µm, or about 75 µm. In particular embodiments, the separation channel 140 is a capillary tube and/or a microfluidic channel. Additional suitable separation channels 140 are known to those of ordinary skill in the art.

In one or more embodiments, the inlet 144 functions as an outlet and/or the outlet functions as an inlet. In further embodiments, the inlet 144 functions to allow LE fluid, such as, e.g., LE solution, to enter and/or exit the separation channel 140. Similarly, in further embodiments, the outlet functions to allow TE fluid, such as, e.g., TE solution, sample, and/or DNA sensor molecules to enter and exit the separation channel.

Figure 6:
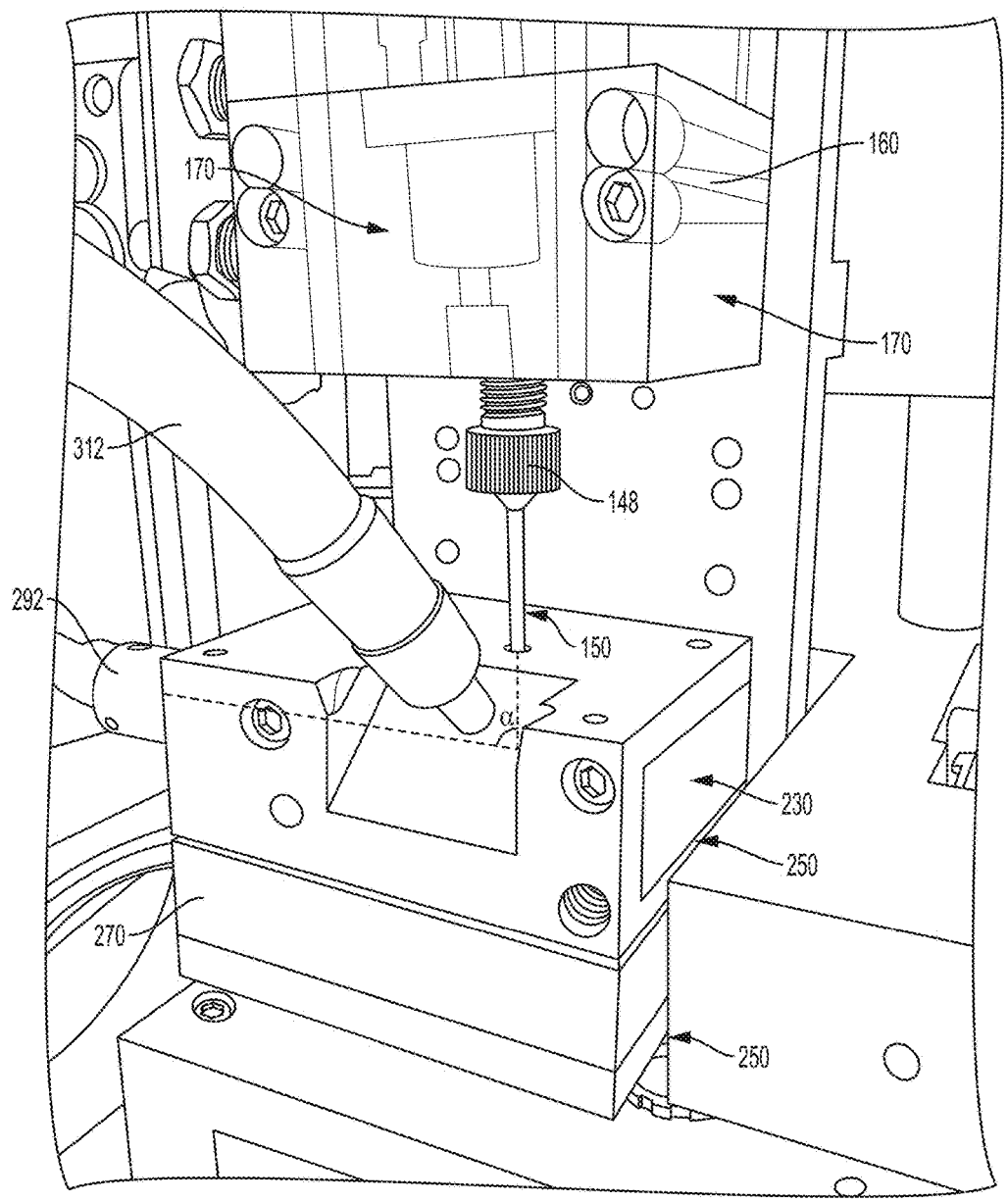
FIG. 6 is a front perspective view of at least a portion of an electrophoretic assembly having a bundle of separation channels illuminated by at least one light source according to embodiments described herein.
Figure 8:
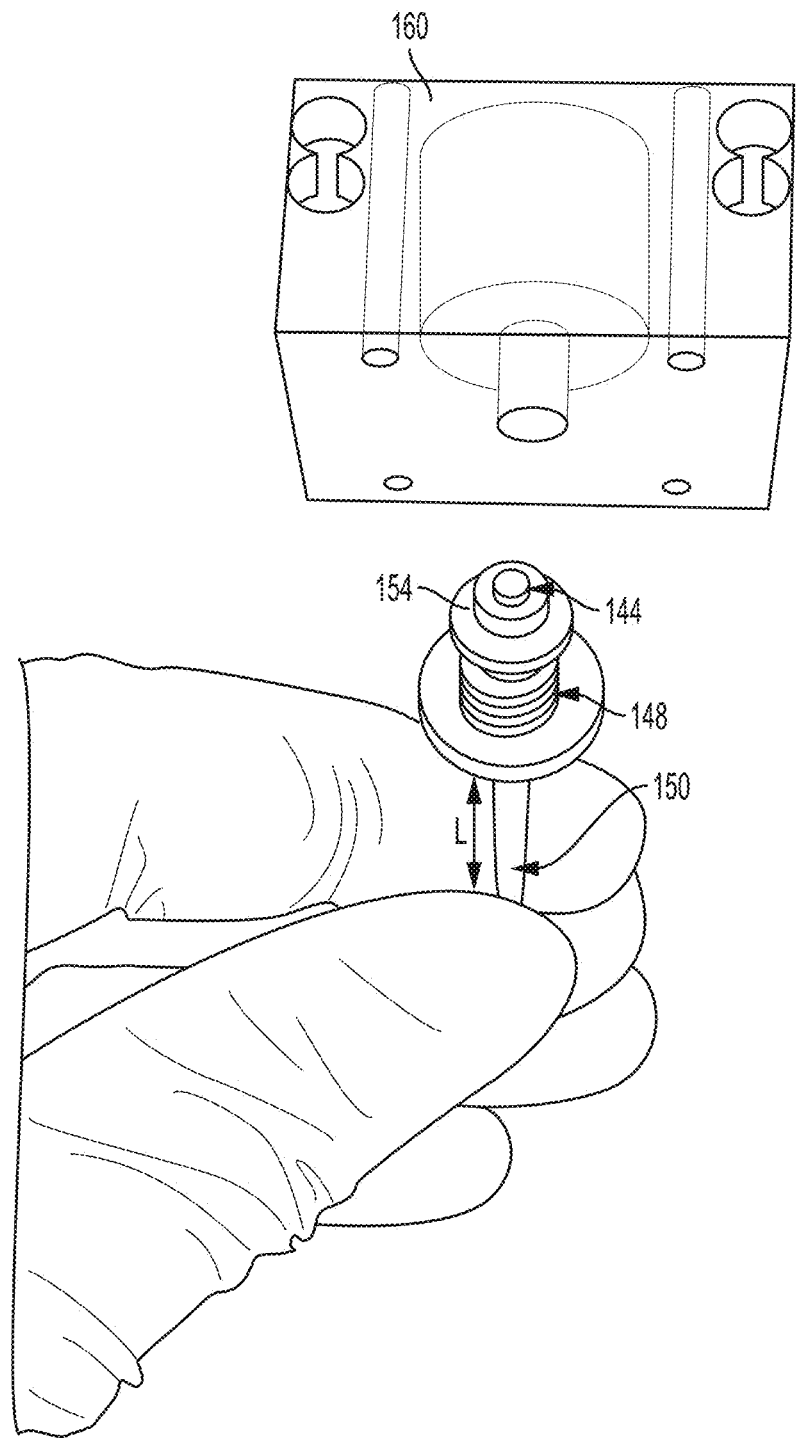
FIG. 8 is a top perspective view of a bundle of separation channels separated from a leading electrolyte reservoir according to embodiments described herein.

Referring specifically to FIGS. 6 and 8, in some embodiments, the separation unit 130 includes a plurality of separation channels 140. In embodiments, the plurality of separation channels 140 form a bundle of separation channels 150. In particular embodiments, the separation unit 130 includes from about 2 to about 200 separation channels 140, or from about 5 to about 100 separation channels 140, or from about 10 to about 50 separation channels 140, or about 20 separation channels 140. In one specific embodiment, the separation unit 130 includes 19 separation channels 140. In further embodiments, the separation unit 130 includes 19 separation channels 140 having respective lengths L of from about 1 cm to about 20 cm, or from about 5 cm to about 15 cm, or about 10 cm. In one or more embodiments, the separation channels 140 are arranged, such as, e.g., in a bundle, such that the lengths L of each of the separation channels 140 are substantially parallel to one another and/or such that the inlets 144 and the outlets of each of the separation channels 140 are substantially aligned.

Referring now to FIGS. 2, 5, and 7-8, in one or more embodiments, the separation unit 130 includes a leading electrolyte reservoir 160 in fluidic communication with the at least one separation channel 140. In some embodiments, the leading electrolyte reservoir 160 is in continuous, open fluidic communication with the at least one separation channel 140. In embodiments, the leading electrolyte reservoir 160 includes a lower housing 162, a cavity (i.e., hole) 164 defined by the lower housing 162, and an upper housing 166 releasably and/or movably attached to, connected to, and/or attachable to the lower housing 162 for enclosing the cavity 164. In some embodiments, the upper housing 166 is releasably and/or movably attached to or connected to the lower housing 162 such that the cavity 164 defined therein may be accessed, such as for, e.g., inserting LE solution therein. In some embodiments, the lower housing 162 includes an upper surface 168, side surfaces 170, and a lower surface 172. In further embodiments, the upper surface 168 defines the cavity 164. In one or more embodiments, the cavity 164 extends from the upper surface 168 to the lower surface 172 of the lower housing 162, such that, e.g., a LE solution may flow through the leading electrolyte reservoir 160 into a separation channel 140 and/or bundle of separation channels releasably attached or connected thereto. In embodiments, the cavity 164 includes an upper surface diameter at the upper surface 168 of the lower housing 162 and a lower surface at the lower surface 172 of the lower housing 162. The upper surface diameter may be equal to the lower surface diameter. In embodiments, the diameter of the upper surface and the lower surface may be equal and may be from about 0.5 to about 2 cm, or from about 1 to about 1.5 cm, or about 1 cm. In further embodiments, the cavity 164 may be substantially cylindrical. In specific embodiments, the upper housing 166 is formed from a poly(sulfone).

As shown in FIGS. 5-8, the separation channel 140 and/or bundle of separation channels 150 is releasably attached to, connected to, and/or attachable to the lower housing 162. More specifically, the separation channel 140 and/or bundle of separation channels 150 is releasably attached to, connected to, and/or attachable to the cavity 164 defined by the lower housing 162 via an adapter 148, such as, e.g., an adapter nut and/or a one-piece fitting, commercially available from LabSmith (Livermore, Calif.), connected to a port connector (not shown) within the cavity 164. In embodiments, the separation channel 140 and/or bundle of separation channels are releasably attached to and/or connected to the lower housing 162 such that it may be readily interchanged, such as, e.g., in between GEITP experiments. In some embodiments, the port connector is adhered, such as, e.g., via glue and/or epoxy, to the cavity 164 of the lower housing 162. In embodiments, the adapter 148 further includes a flangeless ferrule 154. In some embodiments, the lower surface diameter (not shown) of the cavity 164 is shaped and/or sized to accommodate the adapter 148, port connector, and/or flangeless ferrule 154.

In one or more embodiments wherein the separation channel 140 and/or the bundle of separation channels 150 is releasably connected to the lower housing 162 via the adapter 148, the port connector, and/or the flangeless ferrule 154, the at least one separation channel 140 and/or the bundle of separation channels 150 is positioned in a vertical orientation relative to the lower surface 172 of the lower housing 162. More specifically, in such vertical orientation, the length L of the separation channel 140 or the lengths L of the bundle of separation channels 150 may be positioned substantially perpendicular to or perpendicular to the lower surface 172 of the lower housing 162 (and/or to a horizontal plane parallel to the lower surface 172 of the lower housing 162). For example, in some embodiments, the length L of the separation channel 140 or the lengths L of the bundle of separation channels 150 is positioned substantially parallel to the Z axis (as indicated by the X, Y, and Z coordinates in FIG. 1). Such vertical positioning and/or orientation of the separation channel 140 and/or bundle of separation channels 150 is operable to prevent contamination thereof during GEITP, to cleanly deliver charged analytes, such as, e.g., DNA, to a delivery reservoir in the sampling assembly 350 (as described in greater detail below), wherein a horizontal orientation would not provide for clean delivery out of the separation channel as fluid may be re-introduced into a horizontal separation channel during delivery, and to provide automated GEITP.

In further embodiments, the separation channel 140 or bundle of separation channels 150 is releasably connected to the lower housing 162 such that at least a portion of the separation channel 140 or the bundle of separation channels 150 extends into the cavity 164 such that the separation channel 140 or bundle of separation channels 150 is in selective fluidic communication with the leading electrolyte reservoir 160. More specifically, in some embodiments, the inlet 144 of the separation channel 140 or the inlets 144 of the bundle of separation channels 150 extend into the cavity 164 such that the separation channel 140 or bundle of separation channels 150 is in selective fluidic communication with the leading electrolyte reservoir 160. In this way, LE fluid may flow from the leading electrolyte reservoir 160 through the inlet(s) 144 of the separation channel 140 or bundle of separation channels 150 for the GEITP when the separation channel 140 or bundle of separation channels 150 is in open fluidic communication with the leading electrolyte reservoir 160.

Figure 7:
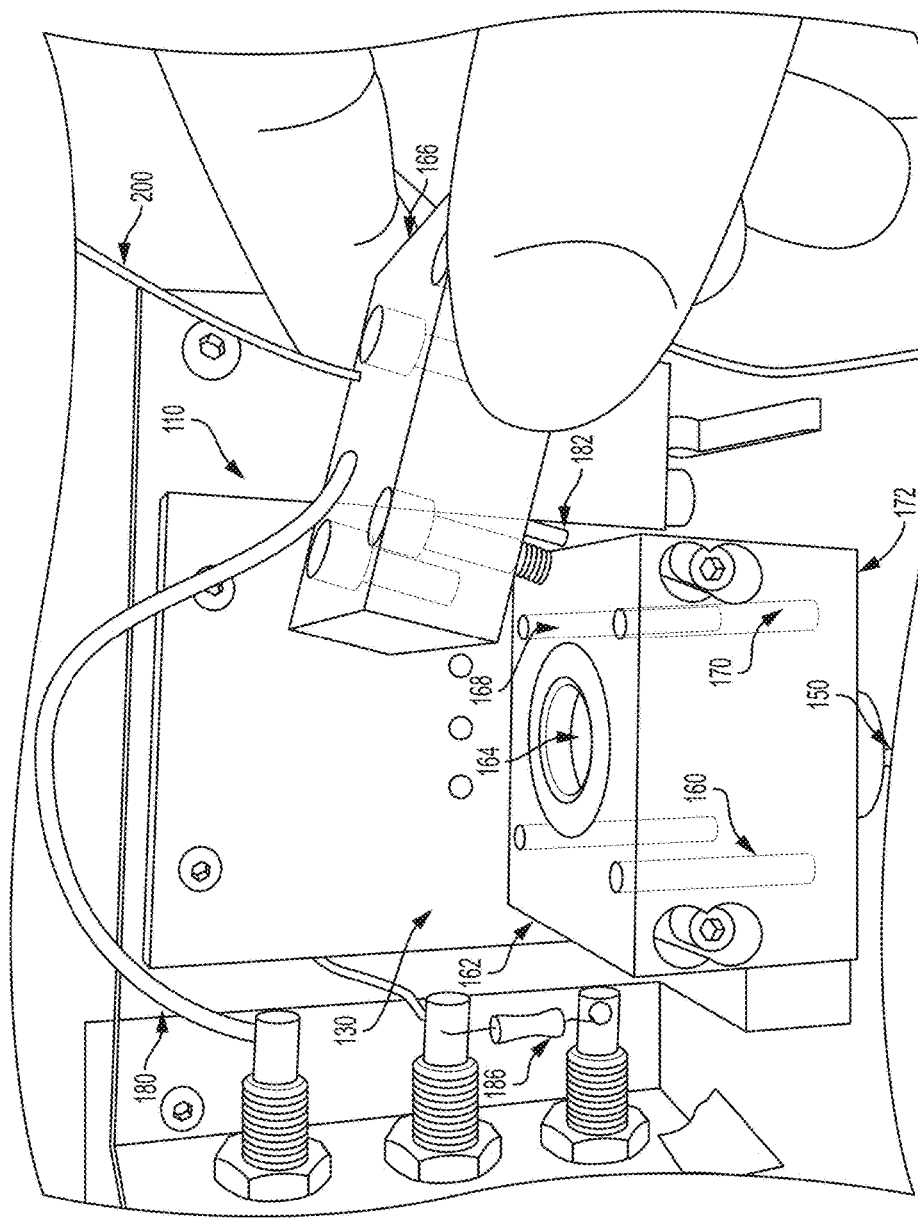
FIG. 7 is a front perspective view of an upper housing of a leading electrolyte reservoir separated from a lower housing of the leading electrolyte reservoir according to embodiments described herein.
Figure 9:
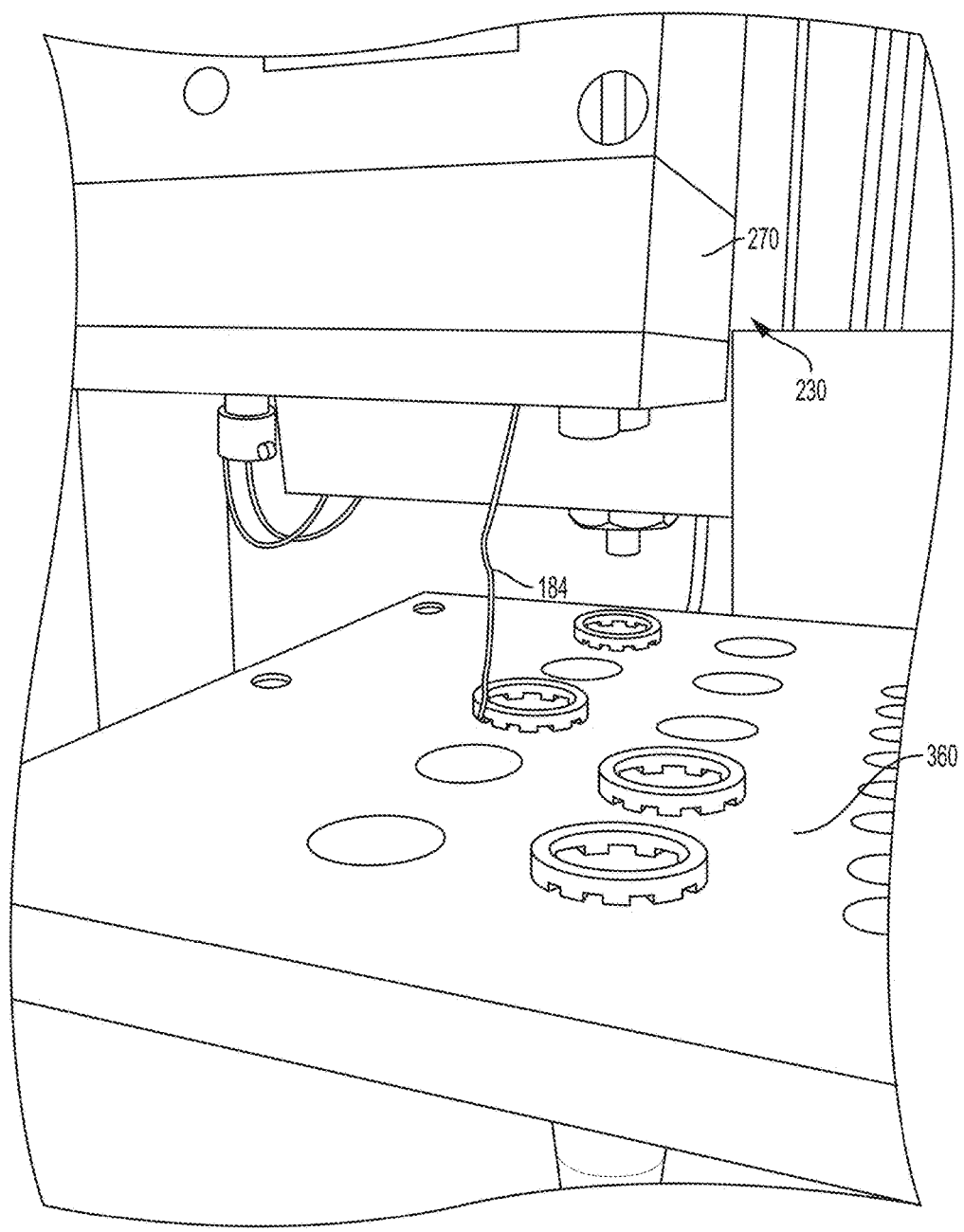
FIG. 9 is a front perspective view of at least a portion of a detection unit and a sampling assembly according to embodiments described herein.
Figure 10:
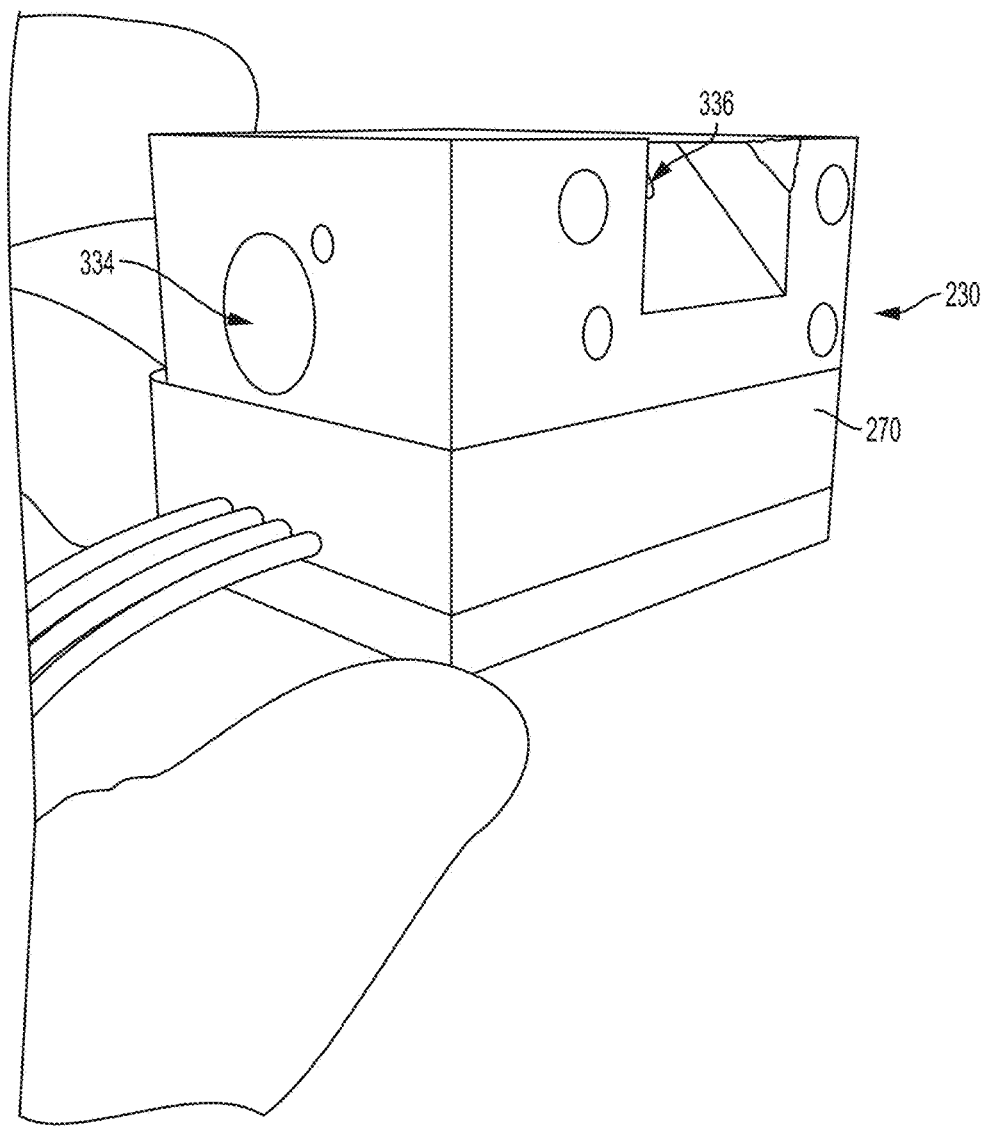
FIG. 10 is a front perspective view of at least a portion of a detection unit separated from a gradient elution isotachophoretic apparatus according to embodiments described herein.
Figure 11:
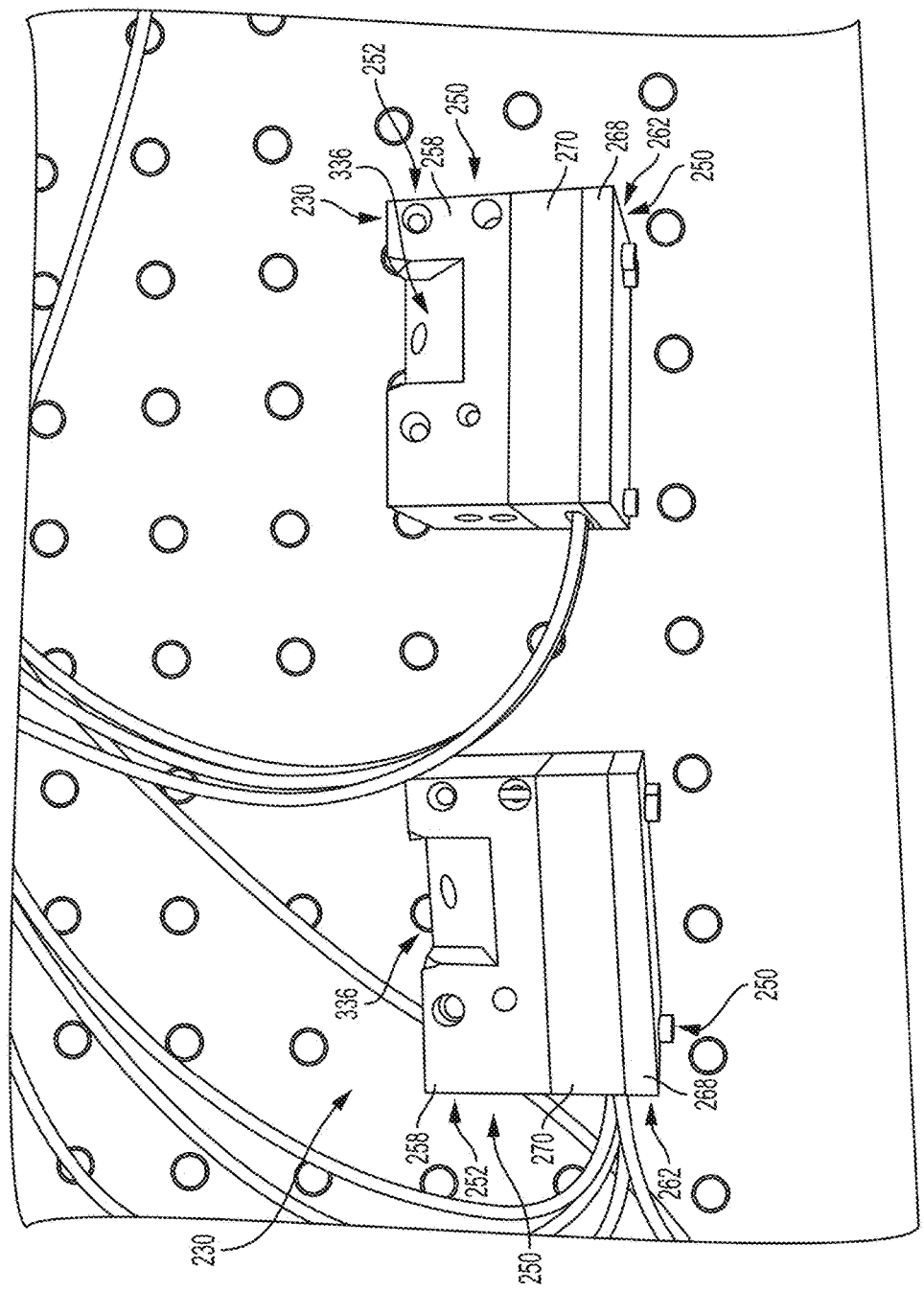
FIG. 11 is a front view of (A) at least a portion of a detection unit for use with a single separation channel according to embodiments described herein (left), and (B) at least a portion of a detection unit for use with a bundle of separation channels according to embodiments described herein (right)

Referring specifically to FIGS. 1-2, 7, 9, and 15, in some embodiments, the separation unit 130 includes a voltage supply device 180 electrically connected and/or communicatively coupled to the separation channel 140 or the bundle of separation channels 150 and electrically connected and/or communicatively coupled to a power source (not shown). In further embodiments, the voltage supply device 180 is electrically connected and/or communicatively coupled to the separation channel 140 or the bundle of separation channels 150 via LE fluid in the leading electrolyte reservoir 160 and via fluid, such as, e.g., LE solution, in the separation channel 140 or bundle of separation channels 150. In some embodiments, the voltage supply device 180 is a high voltage supply device 180 configured to provide a high voltage for GEITP. Referring to FIGS. 7 and 9, in some embodiments, the voltage supply device 180 includes a high voltage electrode 182 electrically connected and/or communicatively coupled to the leading electrolyte reservoir 160 and/or a ground electrode 184 electrically connected and/or communicatively coupled to sample 372 (described in greater detail below).

In some embodiments, the high voltage electrode 182 is configured to contact leading electrolyte fluid in the leading electrolyte reservoir 160, in order to provide a voltage thereto. In this way, the high voltage electrode 182 may be electrically connected and/or communicatively coupled to the separation channel 140 or bundle of separation channels 150 via LE fluid in the leading electrolyte reservoir 160 and via fluid, such as, e.g., LE solution, in the separation channel 140 or bundle of separation channels 150. In some embodiments, the ground electrode 184 is configured to contact specimen fluid in the sample 372.

Additionally, the high voltage electrode 182 may provide a polarity, such as, e.g., positive or negative, dependent upon the polarity of the charged analytes for GEITP. Thus, the polarity of the high voltage electrode 182 may be selected based upon the polarity of the charged analytes. For example, in some embodiments, where the charged analytes are negative, the high voltage electrode 182 may be positive. Similarly, where the charged analytes are positive, the high voltage electrode 182 may be negative. In this way, the voltage supply device 180 is configured to control the direction of the flow of the charged molecules during GEITP. Suitable voltage supply devices 180 are known to those of ordinary skill in the art.

Referring to FIG. 7, in some embodiments, the voltage supply device 180 includes a resistor 186. In some embodiments, the resistor 186 is electrically connected and/or communicatively coupled to the high voltage electrode 182 and/or the ground electrode 184. In embodiments, the resistor 186 is in series with the at least one separation channel 140 or the bundle of separation channels 150.

Figure 23:
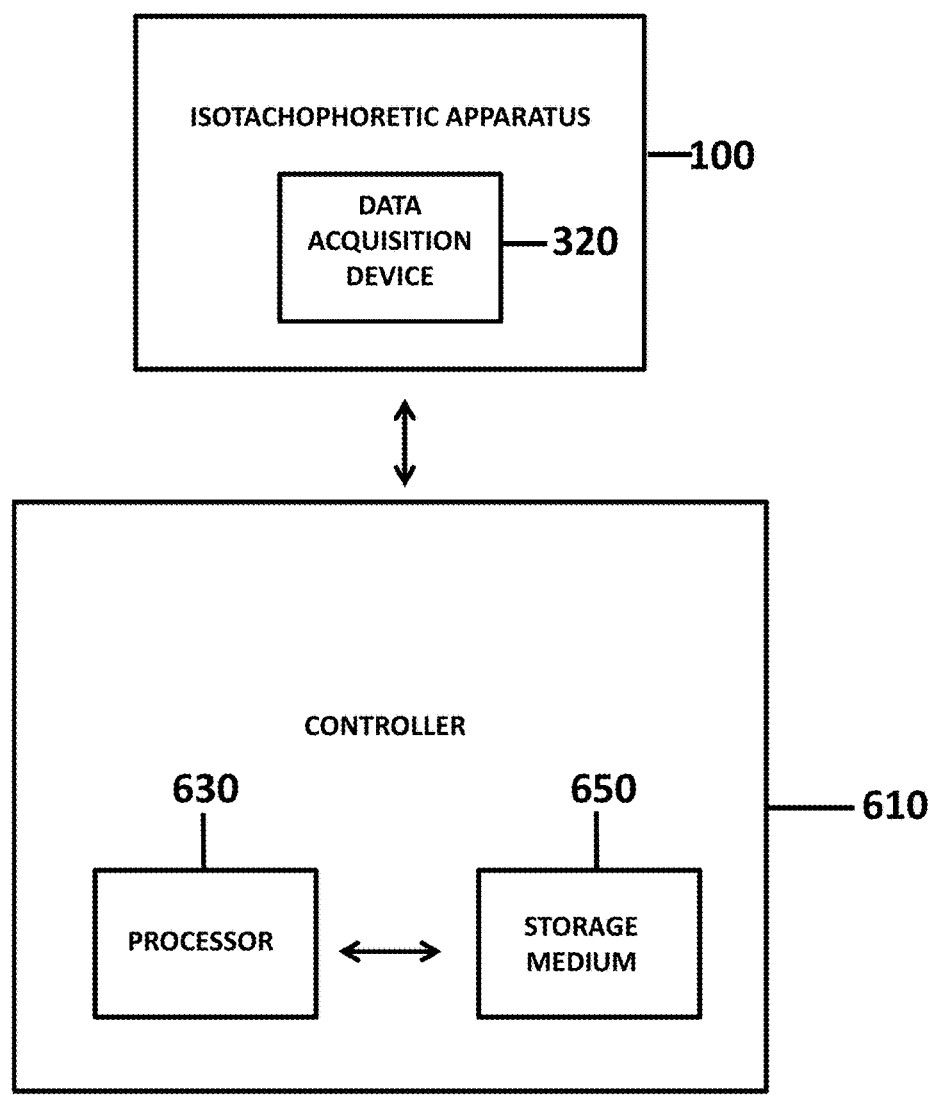
FIG. 23 is a schematic illustration of a system for performing gradient elution isotachophoresis, wherein double headed arrows in between the processor and the storage medium of the controller and in between the isotachophoretic apparatus and the controller represent a communicatively coupled relationship.

Referring to FIGS. 7 and 23, in some embodiments, the high voltage electrode 182 and the ground electrode 184 are configured to detect current of fluid, such as, e.g., LE fluid, present in the separation channel 140 and/or in the bundle of separation channels 150 via use of a current detection device 320, such as, e.g., a data acquisition device 320. More specifically, the high voltage electrode 182 and the ground electrode 184 is configured to detect current of fluid present in the separation channel 140 and/or in the bundle of separation channels 150 during GEITP. In some particular embodiments, the current in the fluid in the separation channel 140 and/or bundle of separation channels 150 is detected via measuring and/or monitoring with a current detection device 320, such as, e.g., a data acquisition device 320, a voltage drop across the resistor 186. In some embodiments, the current data acquisition device 320 includes an input channel and an analog-to-digital converter. However, the current in the fluid in the separation channel 140 and/or in the bundle of separation channels 150 may be measured, monitored, and/or detected via any methods known to those of ordinary skill in the art. For example, the current may be measured via suitable current detection devices 320 known to those of ordinary skill in the art. In embodiments, the current detection device 320 is communicatively coupled to the voltage detection device.

Figure 2:
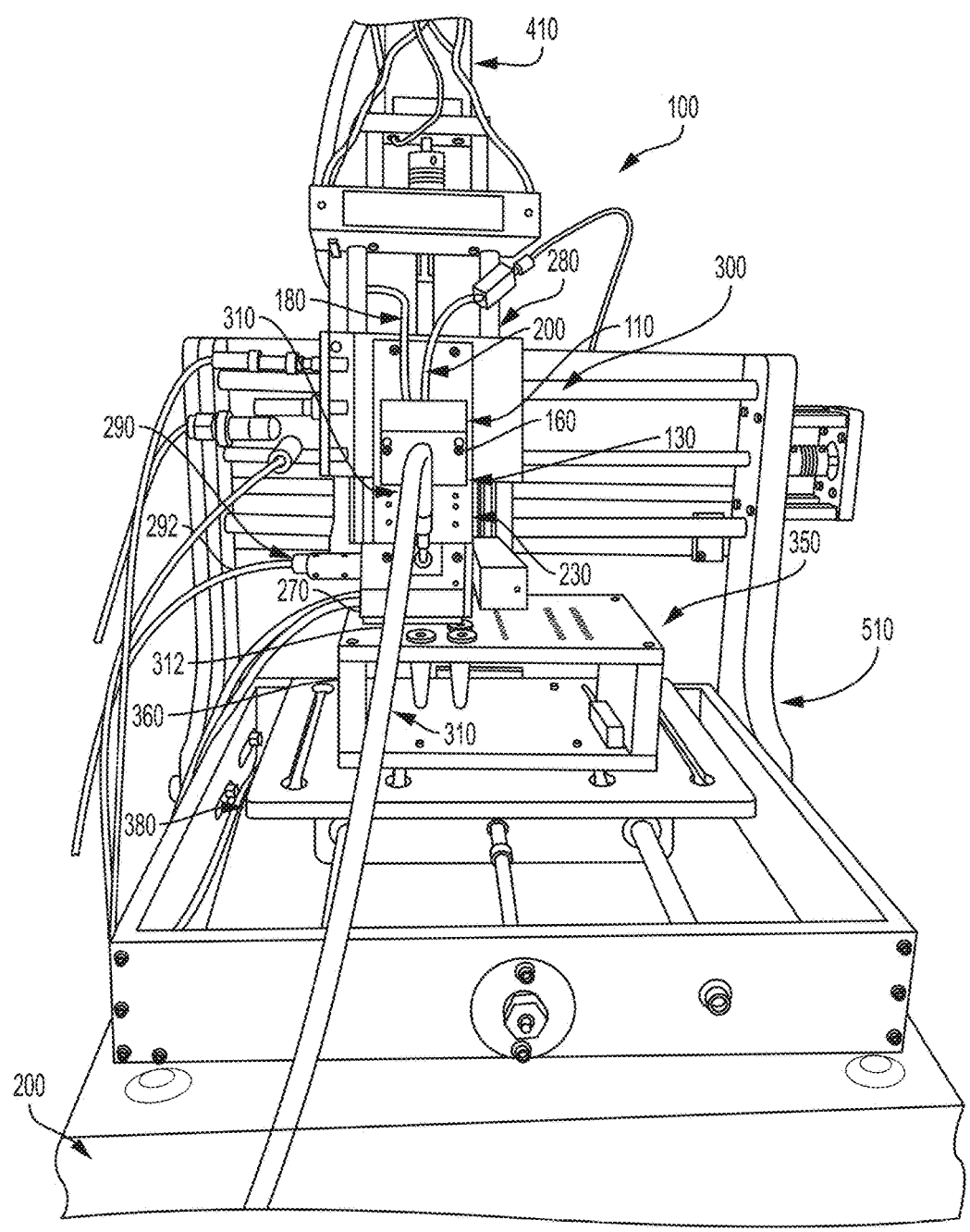
FIG. 2 is a front view of a gradient elution isotachophoretic apparatus according to embodiments described herein.

Referring to FIGS. 1-2 and 7, in some embodiments, the separation unit 130 includes at least one pressure control device 200 connected to the leading electrolyte reservoir 160. In some embodiments, the pressure control device 200 is fluidly connected to the leading electrolyte reservoir 160, in order to provide pressure control thereto. In further embodiments, the pressure control device 200 is connected to headspace, such as, e.g., above the cavity 164, of the leading electrolyte reservoir 160, in order to provide pressure control thereto. The pressure control device 200 is configured to create a variable pressure-driven counterflow for GEITP. In some embodiments, the pressure control device 200 is configured to create a pressure differential across the inlet 144 and the outlet of the separation channel 140 and/or bundle of separation channels 150. In embodiments, the pressure differential across the inlet 144 and the outlet of the separation channel 140 varies with time throughout the GEITP such that charged analytes of interest may be selectively and/or sequentially separated, purified, concentrated, quantified, and/or extracted from a sample and/or such that contaminants may be excluded therefrom. In particular embodiments, the pressure control device 200 creates a pressure differential of from about −20,000 Pa to about 20,000 Pa, or from about −10,000 Pa to about 10,000 Pa, or from about −7,000 Pa to about 7,000 Pa.

Suitable pressure control devices 200 include, but should not be limited to, pumping devices, such as, e.g., a syringe pump. However, additional suitable pressure control devices 200 are known to those of ordinary skill in the art. In some embodiments, the pumping device is accommodated by and/or within the support structure 510 (described in greater detail below). In some embodiments, the pressure control device 200 further includes a pressure detection device (not shown), such as, e.g., a bidirectional pressure gauge (not shown) communicatively coupled to the leading electrolyte reservoir 160. In some embodiments, the bidirectional pressure gauge is accommodated by and/or within the support structure 510. Suitable pressure detection devices are known to those of ordinary skill in the art. Suitable bidirectional pressure gauges are commercially available from Omega Engineering (Stamford, Conn.).

Referring to FIGS. 1-4, 7, 9, and 11, in one or more embodiments, the electrophoretic assembly 110 includes a detection unit 230 communicatively coupled to the separation unit 130. In embodiments, the detection unit 230 includes a support structure 250, a conductivity detection device 270 attached to, connected to, attachable to and/or accommodated by the support structure 250 and communicatively coupled to the separation channel 140, at least one light source 290 attached to, connected to, attachable to, and/or accommodated by the support structure 250, and/or a light source detection device 310 attached to, connected to, attachable to, and/or accommodated by the support structure 250.

Referring to FIGS. 11-14, in some embodiments, the detection unit 230 includes a support structure 250. In some embodiments, the support structure 250 includes an upper portion 252 and a lower portion 262. In some embodiments, the upper portion 252 includes an upper surface 256, side surfaces 258, and a lower surface (not shown). In embodiments, the side surfaces 258 include a first side surface, a second side surface adjacent to the first side surface, a third side surface adjacent to the second side surface, and a fourth side surface adjacent to the third side surface and the first side surface. In embodiments, the first side surface and the third side surface are substantially parallel, and the second side surface and the fourth side surface are substantially parallel. In further embodiments, the second side surface and the fourth side surface are substantially normal to the first side surface and the third side surface. In one or more embodiments, the lower portion 262 includes an upper surface (not shown), a lower surface 266, and side surfaces 268. In one or more embodiments, the support structure 250 provides an interface for substantial alignment and/or alignment of the conductivity detection device 270, the light source 290, the light source detection device 310, and/or the separation channel 140 (described in greater detail below). In this way, in operation, the conductivity detection device 270 may detect charged analytes present in the at least one separation channel, the light source 290 may direct and/or emit light through the at least one separation channel 140 (as described in greater detail below), exciting fluorescence in charged analytes contacted with sensor molecules present therein (as described in greater detail below), and the light source detection device 310 may detect the fluorescence excited in the at least one separation channel 140 (as described in greater detail below). In some embodiments, the support structure 250 is formed from a polyoxymethylene, i.e., Delrin.

Referring to FIGS. 1-3, 5-6, and 9-11, in some embodiments, the detection unit 230 includes a conductivity detection device 270 attached to, connected to, and/or attachable to the support structure 250 and communicatively coupled to the separation channel 140 and/or bundle of separation channels 150. More specifically, in one or more embodiments, the conductivity detection device 270 is attached to, connected to, attachable to and/or accommodated by the upper portion 252 of the support structure 250 and the lower portion 262 of the support structure 250. In further embodiments, the conductivity detection device 270 is attached to, connected to, attachable to, and/or accommodated by the lower surface (not shown) of the upper portion 252 of the support structure and to the upper surface (not shown) of the lower portion 262 of the support structure 250.

In some embodiments, the conductivity detection device 270 includes ring electrodes. In one or more embodiments, the conductivity detection device 270 defines a cavity (not shown) for accommodating the separation channel 140 and/or bundle of separation channels 150. In some embodiments, the conductivity detection device 270 is communicatively coupled to and/or interfaced with the separation channel 140 and/or bundle of separation channels 150, in order to detect conductivity therethrough. In further embodiments, the conductivity detection device 270 is configured to detect conductivity of fluid present in the separation channel 140 and/or bundle of separation channels 150 during GEITP. Suitable conductivity detection devices 270 include contactless conductivity detectors. However, additional suitable conductivity detection devices 270 are known to those of ordinary skill in the art.

Figure 5:
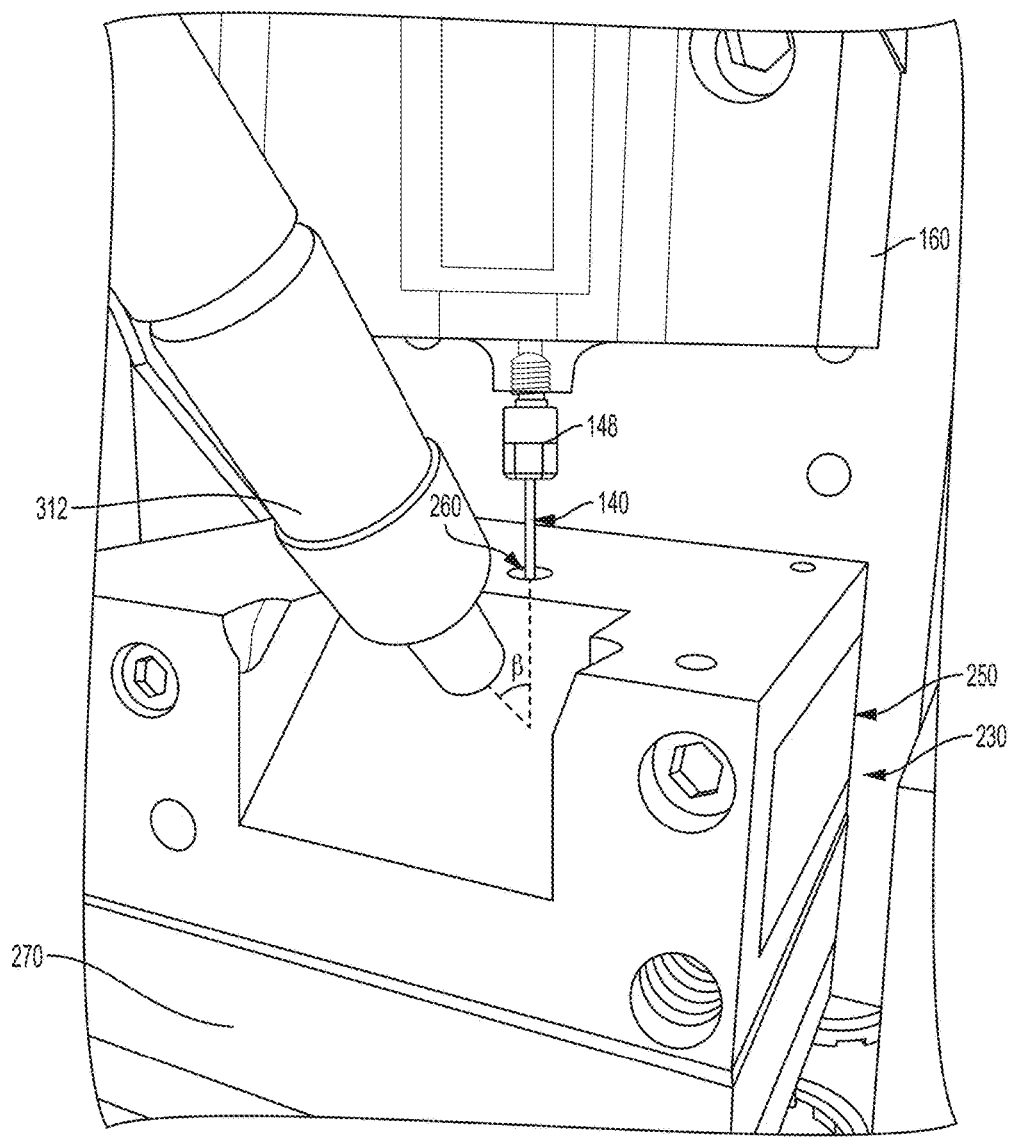
FIG. 5 is a front perspective view of at least a portion of an electrophoretic assembly according to embodiments described herein.

Referring to FIGS. 1 and 5-6, in some embodiments, the detection unit 230 includes a light source 290. In one or more embodiments, the light source 290 is accommodated by the support structure 250. In some embodiments, the light source 290 includes a light source input 292, which is accommodated the support structure 250. More specifically, in some embodiments, the light source 290 is attached to, connected to, attachable to, and/or accommodated by the upper portion 252 of the support structure 250 (described in greater detail below).

In some embodiments, the light source 290 directs and/or emits light through the separation channel 140 and/or bundle of separation channels 150. In one or more embodiments, the light source 290 is configured to direct and/or emit light through fluid in the separation channel 140 and/or bundle of separation channels 150 during GEITP to excite fluorescence therein. For example, in embodiments wherein the charged analytes are DNA and wherein DNA sensor molecules are in contact with and/or intercalated within DNA in the separation channel 140 and/or bundle of separation channels 150 (described in greater detail below), the light source 290 is configured to direct and/or emit light through such fluid during GEITP to excite and/or induce fluorescence therein. In some specific embodiments, the light source 290 is a laser. In some embodiments wherein the light source 290 is a laser, the light source input 292 is a laser-induced fluorescence input 292. However, additional suitable light sources 290 are known to those of ordinary skill in the art.

Referring to FIGS. 1-2, 5-6, and 9-14, in embodiments, the detection unit 230 includes a light source detection device 310. In one or more embodiments, the light source detection device 310 is attached to, connected to, attachable to, and/or accommodated by the support structure 250. More specifically, in some embodiments, the light source detection device 310 (which may include a photomultiplier tube (i.e., PMT) output 312 as described in greater detail below) is accommodated by the upper portion 252 of the support structure 250 (described in greater detail below).

In some embodiments, the light source detection device 310 is configured to detect light and/or fluorescence excited and/or emitted through and/or by fluid in the separation channel 140 and/or bundle of separation channels 150 during GEITP, as previously described with regard to the light source 290. In one or more embodiments, the light source detection device 310 is communicatively coupled to and/or interfaced with the light source 290 and/or the separation channel 140 and/or bundle of separation channels 150, in order to detect light and/or fluorescence excited and/or emitted from the separation channel 140 and/or bundle of separation channels 150, as previously described with regard to the light source 290. In one or more specific embodiments, the light source detection device 310 is photomultiplier tubes, accommodated by the support structure 250. In some embodiments, the light source detection device 310 includes a photomultiplier tube (i.e., PMT) output 312. However, additional suitable light source detection devices 310 are known to those of ordinary skill in the art.

Figure 12:
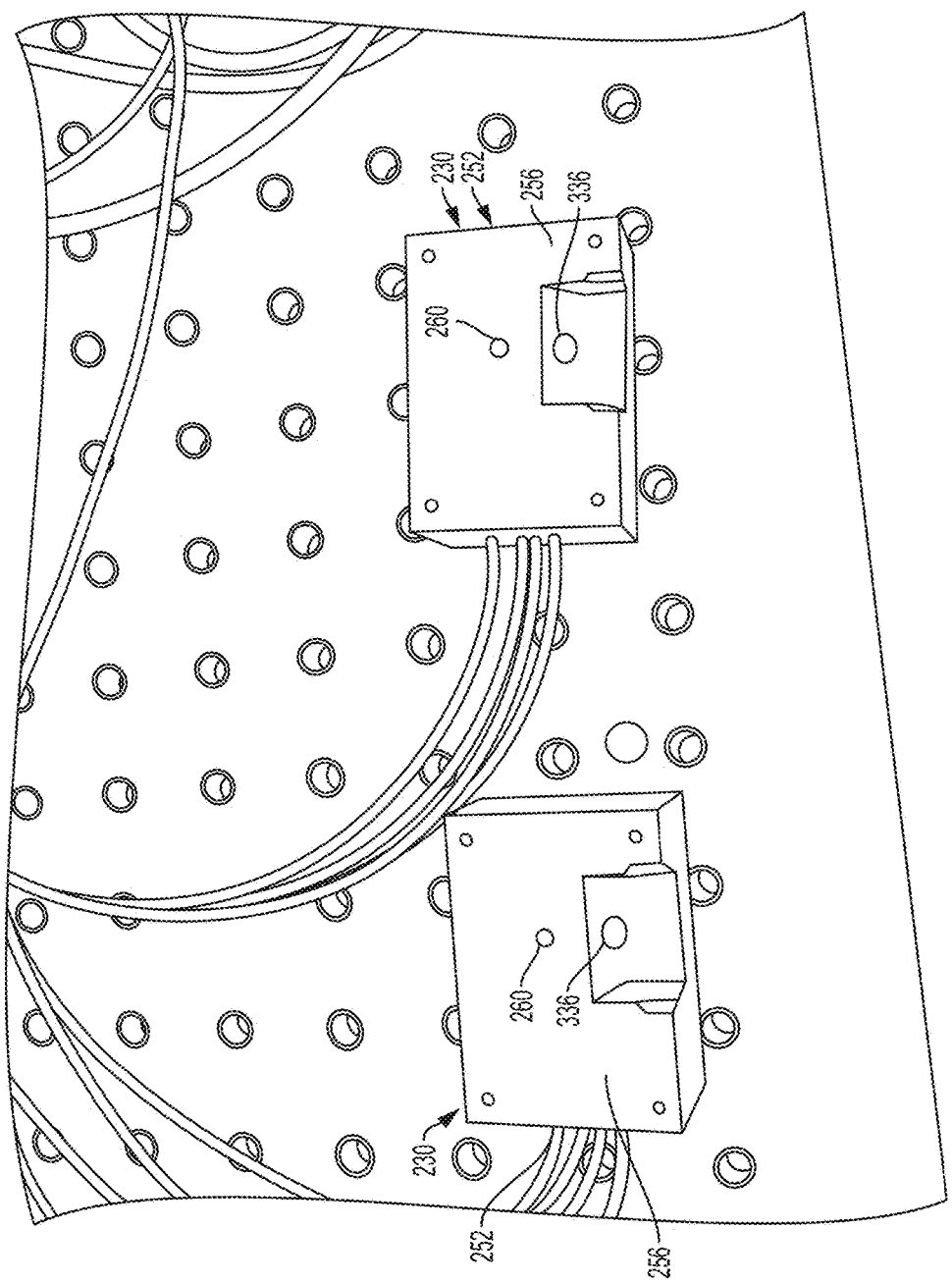
FIG. 12 is a top view of (A) at least a portion of a detection unit for use with a single separation channel according to embodiments described herein (left), and (B) at least a portion of a detection unit for use with a bundle of separation channels according to embodiments described herein (right)
Figure 13:
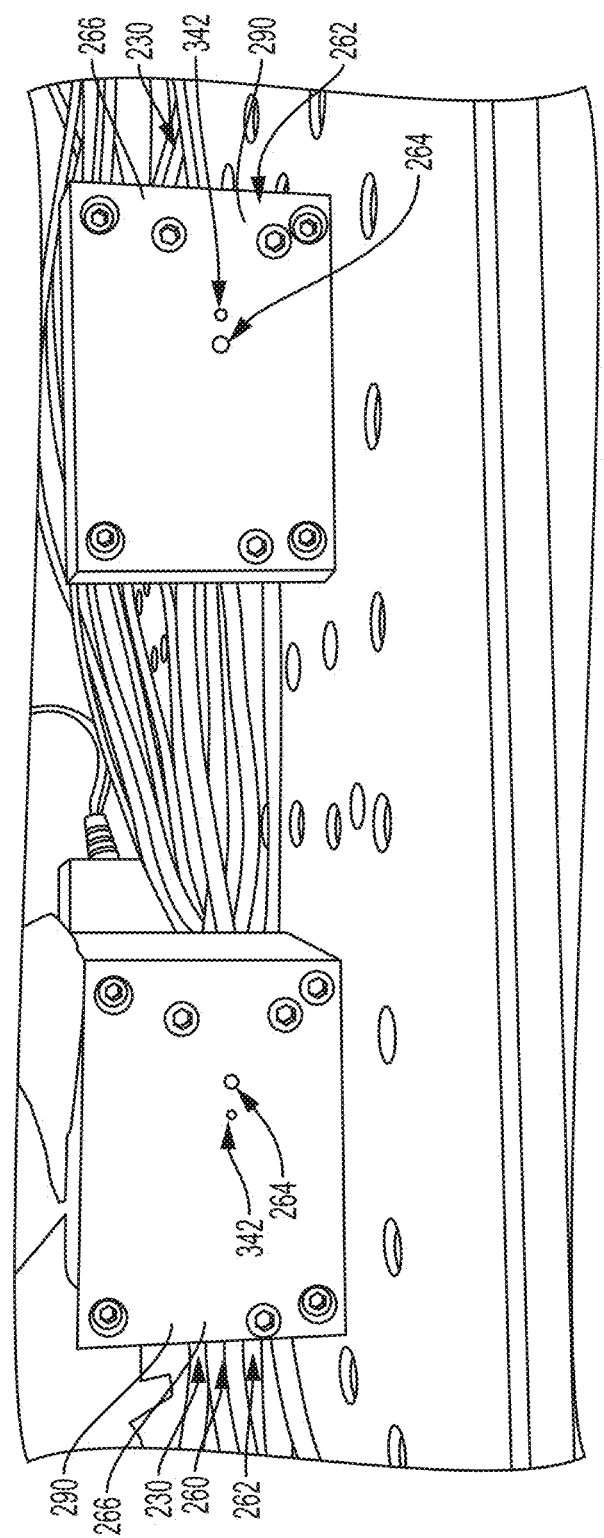
FIG. 13 is a bottom view of (A) at least a portion of a detection unit for use with a single separation channel according to embodiments described herein (left), and (B) at least a portion of a detection unit for use with a bundle of separation channels according to embodiments described herein (right)

Referring to FIGS. 5-6 and 10-14, in some embodiments, the support structure 250 provides an interface for substantial alignment and/or alignment of the conductivity detection device 270, the light source 290, the light source detection device 310, the separation channel 140, the bundle of separation channels 150, the laser-induced fluorescence input 292, the PMT output 312, and/or the ground electrode 184. For example, the support structure 250 defines a separation channel cavity 260, 264, for accommodating the at least one separation channel 140 or bundle of separation channels 150 therein. Referring specifically to FIGS. 5 and 12-13, each of the upper portion 252 and the lower portion 262 of the support structure 250 provides a cavity (i.e., hole) 260, 264, respectively, for accommodating the separation channel 140 and/or bundle of separation channels 150 therethrough. More specifically, each of the upper portion 252, the lower portions 262, and the conductivity detection device 270 provides corresponding cavities through which the separation channel 140 and/or bundle of separation channels 150 may extend therethrough and be accommodated. In this way, at least a portion of the separation channel 140 and/or bundle of separation channels 150 may extend into the cavities 260, 264 of the upper portion 252 and the lower portion 262 and the cavity of the conductivity detection device 270 such that light may be directed and/or emitted therethrough and such that resulting emitted and/or excited fluorescence may be detected therefrom during GEITP.

Figure 14:
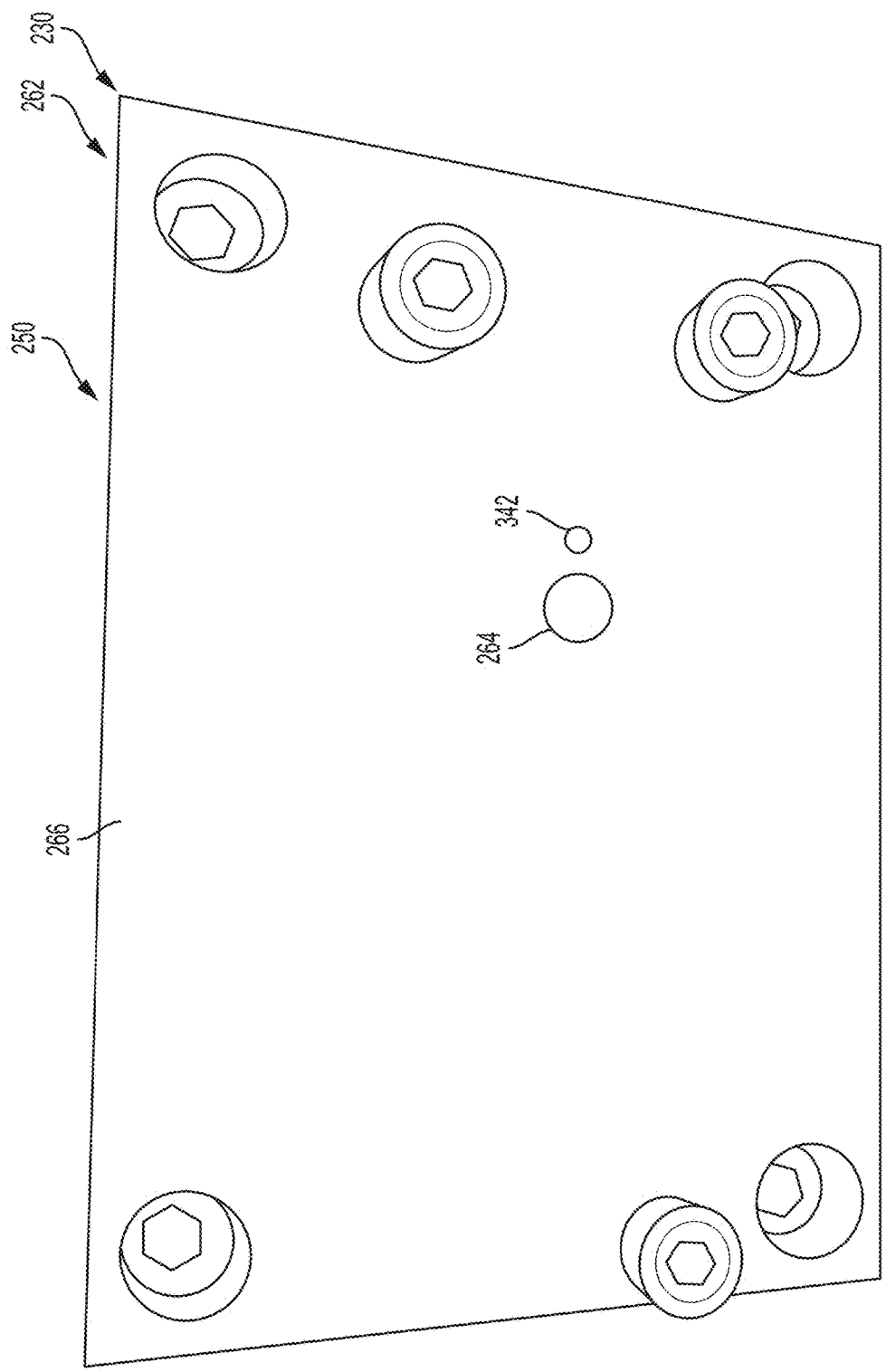
FIG. 14 is a bottom view of at least a portion of a detection unit for use with a bundle of separation channels according to embodiments described herein.
Figure 15:
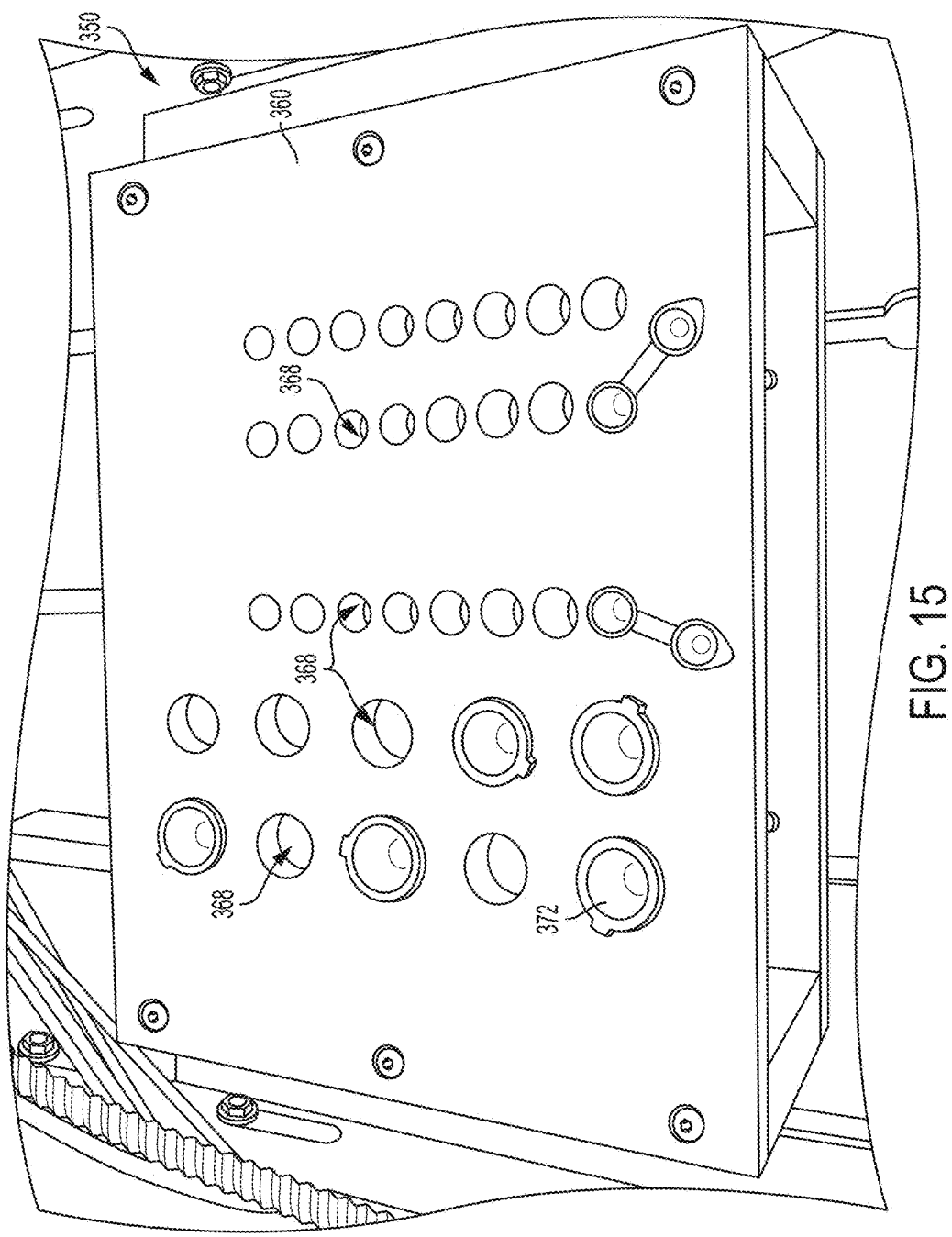
FIG. 15 is a top perspective view of a sampling platform according to embodiments described herein.

In embodiments, the support structure 250 defines a light source cavity 334 for accommodating the light source 290 therein and also defines a light source detection cavity 336 for accommodating the light source detection device 310 therein. As another example, referring specifically to FIG. 10, the support structure 250 provides a cavity 334 for accommodating the input 292, e.g., the laser-induced fluorescence input 292, and a recess and/or cavity 336 for accommodating the PMT output 312. More specifically, adjacent side surfaces 258 of the upper portion 252 of the support structure 250 respectively provide the cavity 334 and the recess and/or cavity 336. In some embodiments, as shown in FIGS. 13-14, the support structure 250 provides a cavity 342 for accommodating the ground electrode 184. The cavities 334, 336, 342, and/or the cavity of the conductivity detection device 270 may respectively correspond substantially in size and/or shape to the laser-induced fluorescence input 292, the PMT output 312, and/or the ground electrode 184.

In embodiments, the light source 290 is accommodated by the support structure 250 at a fluorescence excitation angle α. More specifically, the support structure 250 may define the light source cavity 334 at a fluorescence excitation angle α of from about 30° to about 150°. In embodiments, the fluorescence excitation angle α is about 90°. The fluorescence excitation angle α is formed by intersection of an axis of the light source 290 and a plane bisecting the separation channel cavity 260, 264 and being parallel to the side surfaces 258 of the support structure 250 (and/or to a plane parallel to a vertical axis). In embodiments, the light source detection device 310 is accommodated by the support structure 250 at a fluorescence detection angle β. More specifically, the support structure 250 may define the light source detection cavity 336 at a fluorescence detection angle β of from about 30° to about 150°. In embodiments, the fluorescence detection angle β is about 45°. The fluorescence detection angle β is formed by intersection of an axis of the light source detection device 310 and a plane bisecting the separation channel cavity 260, 264 and being parallel to the side surfaces 258 of the support structure 250 (and/or to a plane parallel to a vertical axis). In this way, the support structure 250 provides an interface such that fluorescence in the separation channel 140 and/or bundle of separation channels 150 may be excited and/or detected.

Figure 3:
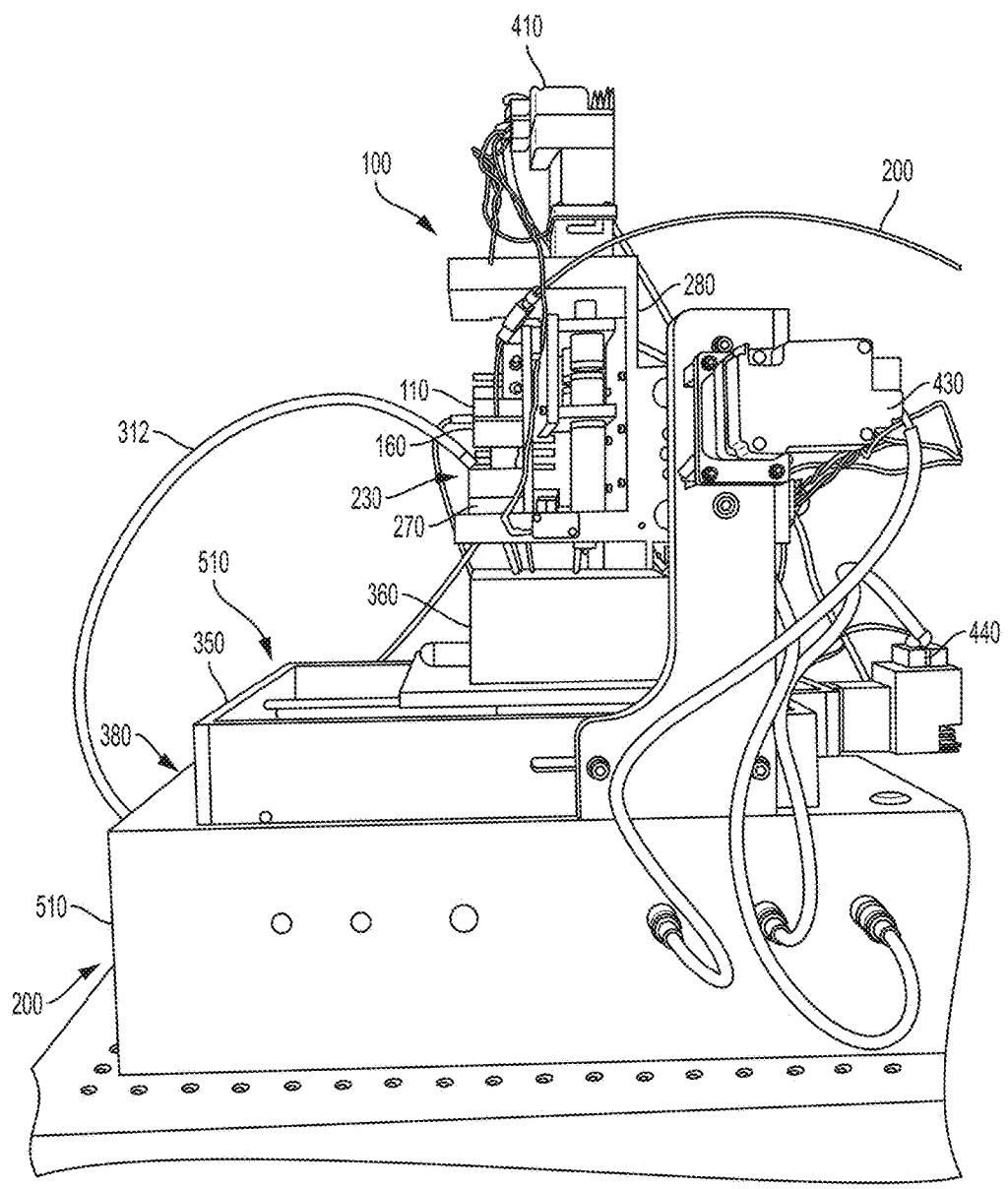
FIG. 3 is a right side view of a gradient elution isotachophoretic apparatus according to embodiments described herein.
Figure 4:
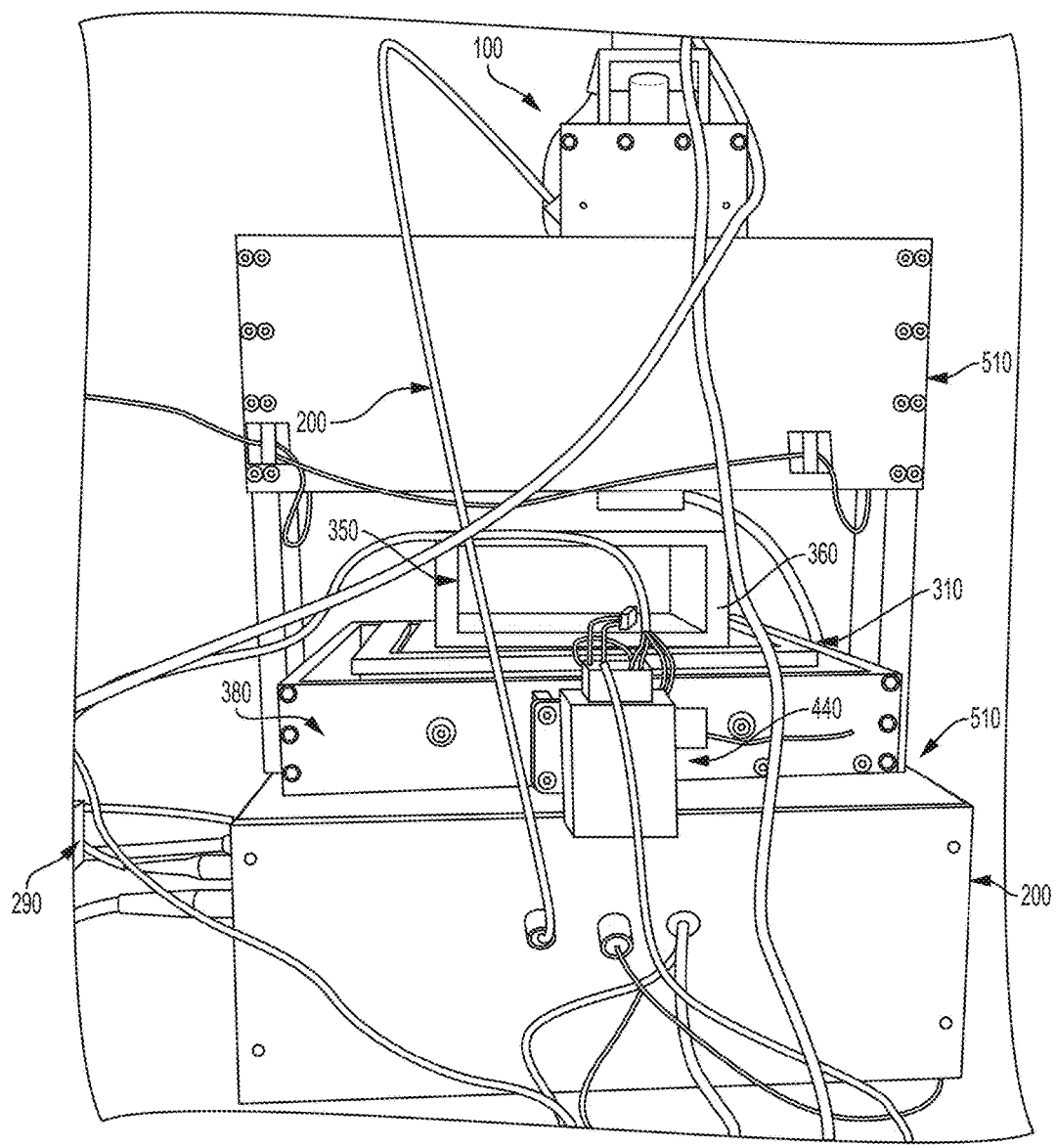
FIG. 4 is a back view of a gradient elution isotachophoretic apparatus according to embodiments described herein.

Referring to FIGS. 1-3, in some embodiments, the electrophoretic assembly 110 is capable of movement. In some embodiments, the electrophoretic assembly 110 is attached to, connected to, and/or attachable to a first moveable support structure 280. The first moveable support structure 280 is configured to provide movement of the electrophoretic assembly 110 in the Z direction (as indicated by the X, Y, and Z coordinates in FIG. 1) via movement thereof. For example, in one or more embodiments, the electrophoretic assembly 110 is capable of upward and/or downward movement via movement of the first moveable support structure 280, relative to a central resting position thereof.

In some embodiments, the first moveable support structure 280 is attached to, connected to, and/or attachable to a second moveable support structure 300. The second moveable support structure 300 is configured to provide movement of the electrophoretic assembly 110 in the X direction (as indicated by the X, Y, and Z coordinates in FIG. 1) via movement thereof. For example, in one or more embodiments, the electrophoretic assembly 110 is capable of movement from side to side, relative to a central resting position thereof.

Referring to FIG. 1, in further embodiments, the first and second moveable support structures 280, 300 are capable of automated movement in the respective the X and Z directions. In some embodiments, each of the first and second moveable support structures 280, 300 is movably attached to a respective support surface 284, 302. The first and second moveable support structures 280, 300 are capable of automated movement in the respective X and Z directions relative to the respective support surfaces 284, 302. In this way, the moveable support structure 280 and the electrophoretic assembly 110 provided thereon are capable of movement in the X and Z directions such that samples 372 (described in greater detail below) may be placed in contact with the outlet of the separation channel 140 and/or outlets of the bundle of separation channels 150.

In some embodiments, the voltage supply device 180, the data acquisition device 320, the pressure control device 200, the pressure detection device (not shown), the conductivity detection device 270, the at least one light source 290, the light source detection device 310, the first, second, and third (described in greater detail below) moveable support structures 280, 300, 380, and/or the first, second, and third (described in greater detail below) motors, 410, 430, 440, are communicatively coupled to a data receiver (not shown) and/or a controller (as described in greater detail below with regard to GEITP systems). It is to be understood that any structures and/or devices previously described herein with regard to the isotachophoretic apparatus 100 may be communicatively coupled to a data receiver and/or the controller, such that the GEITP methods (described in greater detail below) may be fully automated.

Referring to FIGS. 1-3 and 15-16, in one or more embodiments, the isotachophoretic apparatus 100 includes a sampling assembly 350. In further embodiments, the sampling assembly 350 is operably connected to the electrophoretic assembly 110. In embodiments, the sampling assembly 350 is operably connected to the electrophoretic assembly 110 such that samples 372 may be placed in contact with the outlet of the separation channel 140 and/or outlets of the bundle of separation channels 150. In some embodiments, the length L of the separation channel 140 and/or lengths L bundle of separation channels 150 are oriented substantially perpendicular to the horizontal plane of a sampling platform 360 of the sampling assembly 350, such that the samples 372 may be placed in contact with the outlet of the separation channel 140 and/or outlets of the bundle of separation channels 150. In some embodiments, the sampling assembly 350 includes a sampling platform 360 attached to, connected to, and/or attachable to a moveable support structure 380.

Figure 16:
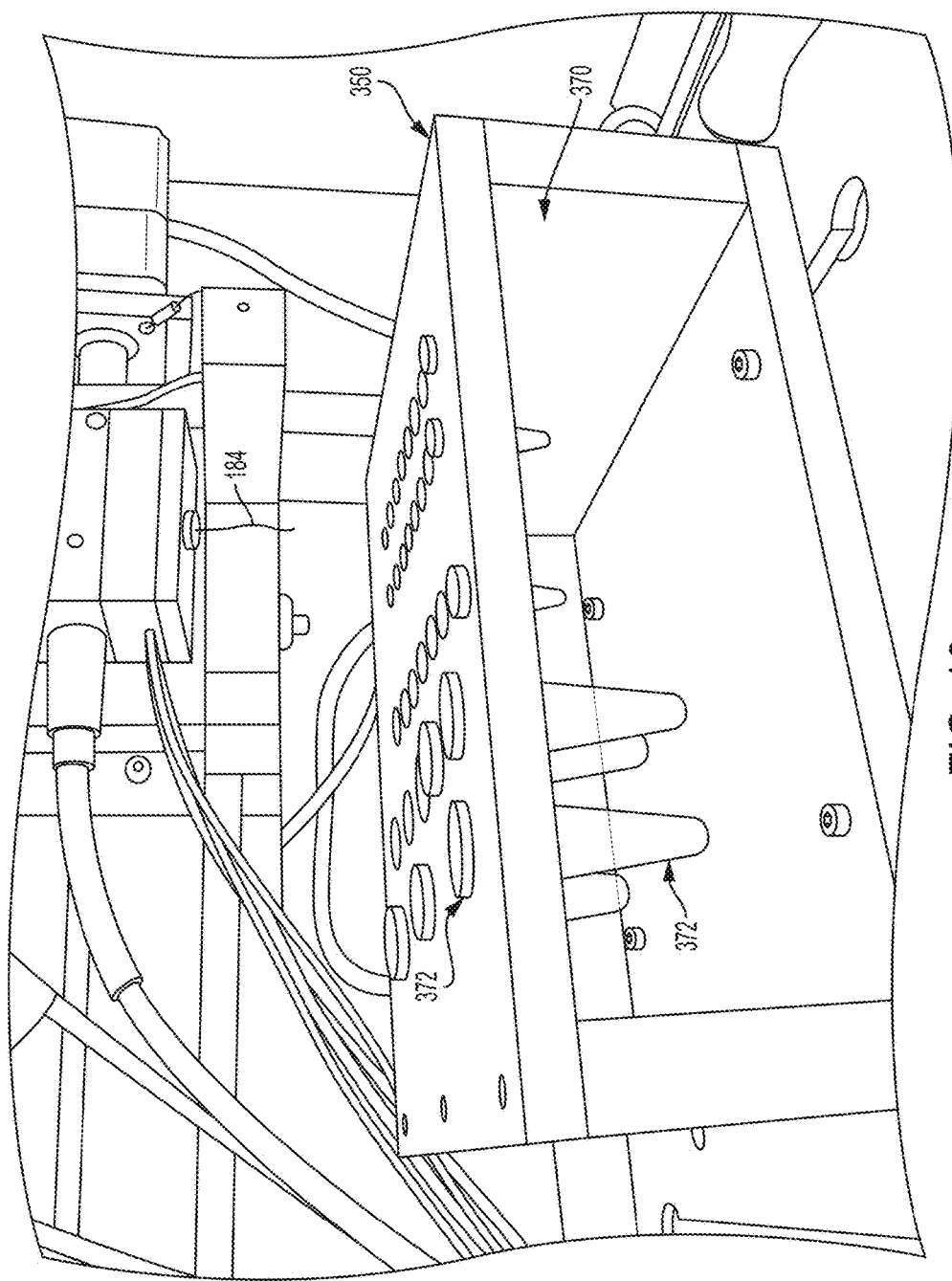
FIG. 16 is a front perspective view of a sampling platform according to embodiments described herein.

Referring to FIGS. 1-2 and 15-16, in one or more embodiments, the sampling assembly 350 includes a sampling platform 360. In embodiments, the sampling assembly 350 is attached to, connected to, and/or attachable to a third moveable support structure 380. In some embodiments, the sampling assembly includes an upper surface 362, side surfaces 364, and a lower surface 366. In further embodiments, the upper surface 362 defines a plurality of cavities (i.e., holes) 368 extending therethrough. The cavities 368 may be configured such that samples 372, such as samples 372 provided in sample reservoirs, such as, e.g., Eppendorf, microcentrifuge, and/or PCR tubes, may be accommodated therein. Examples of suitable samples 372 which may be accommodated by the cavities 368 include, but should not be limited to, sample reservoirs including specimens of interest, pre-treatment reagent reservoirs, buffer reservoirs, and/or delivery reservoirs for delivery of the separated, purified, concentrated, and/or quantified charged analytes. In some embodiments, the cavities 368 have a substantially circular, ovular, oblong, and/or square cross-sectional shape. However, the cavities 368 may have any cross-sectional shape and/or size such that the cavities 368 may accommodate samples 372 therein. In one or more embodiments, as shown in FIG. 16, the sampling assembly defines a space 370 in between the upper surface 362 and the lower surface 366 and the side surfaces 364, such that samples 372 may extend at least partially therethrough and/or be securely accommodated therein.

Referring to FIGS. 1-4, in one or more embodiments, the sampling assembly 350 includes a third moveable support structure 380, i.e., a sampling moveable support structure. The third moveable support structure 380 is configured to provide movement of the sampling platform 360 in the Y direction (as indicated by the X, Y, and Z coordinates in FIG. 1) via movement thereof. For example, in one or more embodiments, the sampling platform 360 is capable of forward and/or backward movement via movement of the third moveable support structure 380, relative to a central resting position thereof.

In further embodiments, the third moveable support structure 380 (as well as the first moveable support in the Z direction and the second moveable support in the Y direction) is capable of automated movement in the Y direction. The third moveable support structure 380 may include a moveable surface 382 movably attached to a support surface 384. In some embodiments, the sampling platform 360 is attached to, connected to, and/or attachable to the moveable surface 382 of the third moveable support structure 380. In this way, the third moveable support structure 380 and the sampling platform 360 provided thereon are capable of moving in the Y direction such that samples 372 may be placed in contact with the outlet of the separation channel 140 and/or outlets of the bundle of separation channels 150 during GEITP.

Referring to FIGS. 1-4, in some embodiments, the isotachophoretic apparatus 100 includes a first, second, and third motor, 410, 430, 440 configured to provide motion of the first, second, and/or third moveable support structures 280, 300, 380. In some embodiments, the first, second, and/or third motor 410, 430, 440, are respectively electrically connected and/or communicatively coupled to the first, second, and/or third moveable support structures 280, 300, 380, in order to provide motion thereto. In embodiments, the first, second, and third moveable support structures 280, 300, 380, and the first, second, and third motors 410, 430, 440, are configured to provide movement, such as, e.g., translation, of the electrophoretic assembly 110 and the sampling assembly 350. Suitable examples of motors for providing motion to the first, second, and/or third moveable support structures 280, 300, 380 include electric and/or hydraulic motors. In some embodiments, the first, second, and/or third motors 410, 430, 440, are stepper motors. However, additional motors for providing movement of the first, second, and third moveable support structures 280, 300, 380 are known to those of ordinary skill in the art.

Referring to FIGS. 1-4, in one or more embodiments, the isotachophoretic apparatus 100 includes a support structure 510 connected to the electrophoretic assembly 110 and/or to the sampling assembly 350. In some embodiments, the support structure 510 accommodates the at least one pumping device, such as, e.g., a syringe pump and at least one pressure detection device (not shown).

Embodiments of isotachophoretic apparatus 100 have been described in detail. Embodiments of systems for performing GEITP to separate charged analytes from samples will be described with reference to FIG. 23. Thereafter, methods for separating, purifying, concentrating, quantifying, and/or extracting charged analytes will be described with reference to FIG. 17.

II. Isotachophoretic System

In one or more embodiments, a system 600 for performing GEITP to separate, purify, concentrate, and/or extract charged analytes is disclosed. In embodiments, the system 600 includes an apparatus 100 for performing GEITP, as previously described herein. For example, the apparatus 100 may include a moveable electrophoretic assembly 110, a sampling assembly 350 operably connected to the moveable electrophoretic assembly 110, and a support structure 510 connected to at least one of the moveable electrophoretic assembly 110 or the sampling assembly 510.

Referring to FIG. 23, in embodiments, the system 600 includes a data receiver and/or controller 610 communicatively coupled (as shown via double headed arrows) to the moveable electrophoretic assembly 110, the sampling assembly 310, and/or the support structure 510. As previously described, the voltage supply device 180, the data acquisition device 320 of the voltage supply devices 180, the pressure control device 200, the pressure detection device (not shown), the conductivity detection device 270, the at least one light source 290, the light source detection device 310, the first, second, and third (described in greater detail below) moveable support structures 280, 300, 380, and/or the first, second, and third (described in greater detail below) motors, 410, 430, 440, may be communicatively coupled to a data receiver (not shown) and/or a controller 610.

In some embodiments, the controller includes a processor 630 and a storage medium 650 containing computer readable and executable instructions which, when executed by the processor, cause the controller to automatically execute a series of steps to control and/or adjust the voltage applied during GEITP and/or the pressure applied during GEITP, and/or to control and/or adjust the positioning of the moveable support structures 280, 300, 380. In this way, the focusing of the charged analytes may be controlled. The processor 630 may be communicatively coupled to the storage medium 650.

In some embodiments, the computer readable and executable instructions execute a series of steps, such as, e.g., steps (1)-(7), as described in greater detail below with regard to methods for separating, purifying, concentrating, quantifying, and/or extracting charged analytes utilizing the isotachophoretic apparatus 100.

Figure 17:
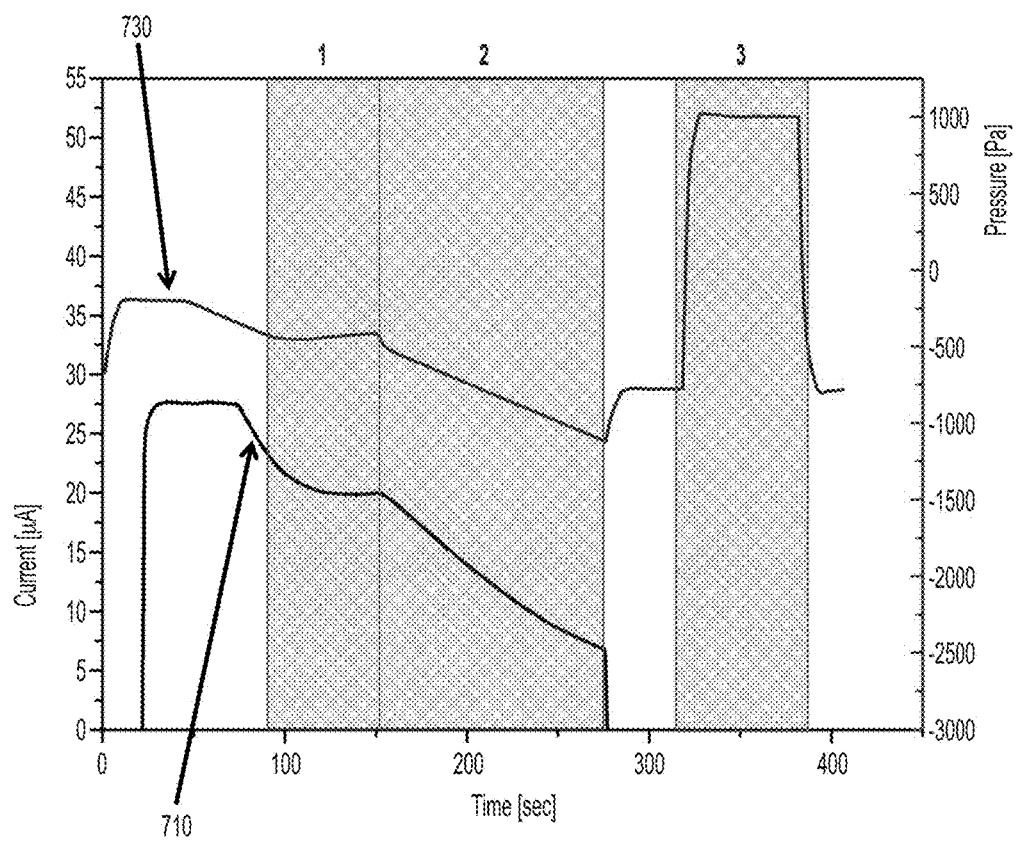
FIG. 17 is graph of Time (sec) with respect to Current (mA) (indicated by black line 710) and Pressure (Pa) (indicated by blue line 730) which depicts (1) focusing of DNA (indicated in shaded grey box 1), (2) incorporation of DNA into a separation channel (indicated in shaded grey box 2), and (3) delivery of DNA (indicated in shaded grey box 3) according to embodiments described herein.

III. Methods for Separating, Purifying, Concentrating, Quantifying, and/or Extracting Charged Analytes In one or more embodiments, methods for separating, purifying, concentrating, quantifying, and/or extracting charged analytes utilizing the isotachophoretic apparatus 100 and/or the isotachophoretic system 600 as previously described herein are disclosed. In one or more embodiments, such methods relate to separating, purifying, concentrating, quantifying, and/or extracting biomolecules, such as, e.g., DNA and/or RNA, from samples, such as, e.g., crude samples, utilizing the isotachophoretic apparatus 100 and/or the isotachophoretic system 600 as previously described herein. In some embodiments, the methods generally include:

(1) optionally pre-treating the separation channel 140 and/or bundle of separation channels 150 (hereinafter, collectively referred to as the separation channel 140);

(2) inserting LE fluid into the separation channel 140;

(3) contacting the separation channel 140 with a sample and TE fluid;

(4) separating, purifying, concentrating, and/or quantifying charged analytes in and/or from the sample via GEITP by:

(a) producing a pressure-driven counterflow of fluid through the separation channel 140;

(b) applying a voltage to the separation channel to produce an electric field to drive electrophoretic migration of charged analytes toward the separation channel 140; and (c) varying with respect to time the pressure-driven counterflow through the separation channel to control focusing and/or separation of the charged analytes via initiation of a pressure ramp (such as is shown in FIG. 17);

(5) optionally directing light through the separation channel to excite fluorescence in the charged analytes;

(6) detecting separated, purified, concentrated, and/or quantified charged analytes in the sample via conductivity detection and/or fluorescence detection (such as is shown in FIG. 17); and/or (7) optionally delivering the charged analytes to a delivery reservoir (such as is shown in FIG. 17).

Performance of steps (1)-(7) may be referred to as a run of GEITP. Additionally, the positioning of the sampling assembly 350 may be adjusted in the Y direction as needed in order to perform any of steps (1)-(7) via movement of the third moveable support structure 380. In some embodiments, the positioning of the sampling assembly 350 may be adjusted prior to, during, and/or after performance of any of steps (1)-(7).

With regard to pre-treating the separation channel 140, in one or more embodiments, such pre-treatment involves rinsing the separation channel 140 with pre-treatment reagents, such as, e.g., distilled water, negatively-charged and/or positively-charged capillary coatings, and/or salmon sperm DNA. In some embodiments, the separation channel 140 is rinsed with pre-treatment reagents by: (1) placing a pre-treatment reagent in a pre-treatment reagent reservoir on the sampling platform 360 in contact with the outlet of the separation channel 140 via movement of the first and/or second moveable support structures 280, 300; and (2) varying the pressure of the headspace in the LE reservoir 160 to achieve insertion of the pre-treatment reagents within the channel (not shown). In embodiments, the separation channel 140 is rinsed with pre-treatment reagents only one time each day. Stated another way, in embodiments, the separation channel 140 is not rinsed with pre-treatment reagents prior to every run of GEITP performed; rather, it may be rinsed with pre-treatment reagents periodically, such as, e.g., one time before each series of GEITP runs performed.

Similarly, varying the pressure of the headspace in the LE reservoir 160 also achieves extraction of the pre-treatment reagents therefrom. Specifically, the pressure may be adjusted, such as, e.g., decreased, to from about −100 Pa about −1200 Pa to achieve insertion of the pre-treatment reagents within the channel (not shown), and may be adjusted, such as, e.g., increased, to from about −200 Pa to about −1000 Pa to achieve extraction of the pre-treatment reagents therefrom. For example, during the pre-treating and/or washing of the separation channel 140, the pressure may initially be about −200 Pa. Once the separation channel 140 has been contacted with the appropriate pre-treatment reagent, the pressure may be decreased to about −1200 Pa for from about 60 seconds to about 300 seconds. In particular embodiments, the pressure was decreased to about −1200 Pa for approximately 300 seconds. In embodiments, the separation channel 140 is then moved to a waste reservoir and the pressure is increased to about −1000 Pa. At the end of the pre-treating and/or washing, the pressure may be adjusted to from about 0 Pa to about −700 Pa. In this pre-treatment step, the separation channel 140 and the electrophoretic assembly 110 may move in the X and/or Z (i.e., in the horizontal and/or vertical) direction via movement of the first and/or second moveable support structures 280, 300. In this way, the separation channel 140 and the electrophoretic assembly 110 may contact varying reservoirs, such as, e.g., pre-treatment reagent reservoirs and waste reservoirs, in the sampling assembly 350.

With regard to inserting LE fluid, such as, e.g., LE solution, into the separation channel 140, in one or more embodiments, such insertion involves varying the pressure to achieve insertion thereof. More specifically, the pressure may be adjusted to from about −700 Pa to about −200 Pa to achieve insertion of the LE fluid from the LE reservoir 160 through the inlet 144 of the separation channel 140 and into the channel thereof (not shown). In some embodiments, following insertion, the pressure may be adjusted, such as, e.g., increased, to a slight positive value and may be regulated at a slight positive value to drive a small flow of the LE fluid into the separation channel 140. Suitable LE fluids include, but should not be limited to, Tris buffers. The LE fluids, such as, e.g., LE buffers, should be selected such that the electrophoretic mobility of the LE fluid is higher than that of the charged analytes. Moreover, where biomolecules, such as, e.g., DNA, RNA, proteins, and/or carbohydrates, are the charged analyte of interest, the LE fluid may include biomolecule sensor molecules, such as, e.g., DNA sensor molecules, RNA sensor molecules, protein sensor molecules, and/or carbohydrate sensor molecules, such as affinity-labeled molecules, which are capable of fluorescing upon contact with biomolecules and excitation thereof. Specific examples of such biomolecule sensor molecules which are capable of fluorescing upon contact with biomolecules are known to those of ordinary skill in the art. Thus, in embodiments wherein the detection unit 230 includes at least one light source 290 and a light source detection device 310, the LE fluid may include biomolecule sensor molecules such that direction and/or emission of light through the separation channel 140 by the light source 290 will excite and/or emit fluorescence of biomolecules present therein which have contacted and/or interacted with biomolecule sensor molecules. As a result of such fluorescence excitation and/or emission, biomolecule analytes may then be detected via fluorescence detection with the light source detection device 310.

With regard to contacting the separation channel 140 with sample and TE fluid, such as, e.g., TE solution, in one or more embodiments, such contacting is achieved by: (1) placing a sample of interest prepared in a TE fluid in a TE reservoir on the sampling platform 360 in contact with the outlet of the separation channel 140 via movement of the first and/or second moveable support structures 280, 300; and (2) varying the pressure of the headspace in the LE reservoir 160 to prevent insertion of the sample and TE fluid within the channel (not shown). In some embodiments, the sample may be treated with lysing agents and/or may be diluted prior to insertion into the separation channel 140. In other embodiments, the sample of interest is prepared in the TE fluid via dissolution and/or slurrying therein. In embodiments, the pressure is adjusted to about −700 Pa to prevent insertion of the sample and TE fluid within the channel. In further embodiments, the sample is not filtered, centrifuged, and/or precipitated prior to insertion into the separation channel 140. Suitable TE fluids include, but should not be limited to, Tris HEPES. The TE fluids, such as, e.g., TE buffers, should be selected such that the electrophoretic mobility of the TE fluid is lower than that of the charged analytes. In this contacting step, the separation channel 140 and the electrophoretic assembly 110 may move in the X and/or Z direction via movement of the first and/or second moveable support structures 280, 300. In this way, the separation channel 140 and the electrophoretic assembly 110 may contact varying reservoirs, such as, e.g., the TE reservoir, in the sampling assembly 350. However, contact between the separation channel 140 and the TE reservoir in the sampling assembly 350 should be maintained continuously from steps (3)-(6) (discussed in greater detail below).

With regard to separating, purifying, concentrating, and/or quantifying charged analytes in the sample via GEITP, as described in U.S. Pat. No. 8,080,144, the contents of which are hereby incorporated by reference in their entirety, GEITP is a fluid-phase electroseparation technique which combines the ability of isotachophoresis (i.e., ITP) to concentrate, such as, e.g., to focus, charged analytes with a controlled, variable pressure-driven counterflow for improved control and selectivity thereof. GEITP allows for high-resolution separations in short separation channel 140 lengths, does not require a discrete injection method, and is fast relative to other electrophoretic methods. During GEITP, electrophoretic mobilities of the LE and TE fluids and/or ions thereof, bracket that of the charged analytes in the sample. In some embodiments, GEITP is performed by: (a) producing a pressure-driven counterflow of fluid through the separation channel 140, (b) applying a voltage to the separation channel 140 to produce an electric field to drive electrophoretic migration of charged analytes toward the separation channel 140, and/or (c) varying with respect to time the pressure-driven counterflow of the LE fluid through the separation channel 140.

With regard to producing a pressure-driven counterflow of fluid through the separation channel, such as, e.g., the LE fluid, the pressure-driven counterflow includes electroosmotic flow (i.e., EOF) and/or controlled, variable pressure-driven flow, i.e., hydrodynamic flow. Thus, the pressure-driven counterflow of the LE fluid may be produced by application of a voltage (such as is described with regard to step (4)(b)), and/or via application of a pressure differential across the inlet 144 and the outlet of the separation channel 140 (such as was previously described). In embodiments, the pressure differential is adjusted to from about −10,000 Pa to about 10,000 Pa, or to from about −5,000 Pa to about 5,000 Pa, or from about −1,000 Pa to about 1,000 Pa, or from about −750 Pa, to about 750 Pa. In particular embodiments, the pressure differential is adjusted to about −700 Pa. In embodiments, the pressure-driven counterflow (i.e., bulk flow) is initially produced such that the charged analytes are prevented from being inserted into the outlet of the separation channel 140 and/or such that LE fluid is introduced into the TE reservoir.

The pressure-driven counterflow may be driven in a direction from the inlet 144 to the outlet of the separation channel 140, or it may be driven in a direction from the outlet to the inlet 144 of the separation channel 140. Typically in GEITP, the pressure-driven counterflow is driven in a direction opposing the net migration of charged analytes through the separation channel 140. Thus, in embodiments, the pressure-driven counterflow is driven in a direction from the inlet 144 to the outlet of the separation channel 140. In embodiments, the pressure-driven counterflow of LE fluid is produced by application of a voltage and application of a pressure differential.

With regard to applying a voltage to the separation channel to drive electrophoretic migration of charged analytes toward the separation channel 140, the polarity of the voltage is dependent upon the direction of the pressure-driven counterflow and the sign of the charged analytes. For example, if the charged analytes are negative in fluid and the pressure-driven counterflow is from the inlet 144 to the outlet of the separation channel 140, the voltage applied to the inlet 144 of the separation channel 140 may be positive relative to the voltage applied to the outlet of the separation channel 140. In embodiments, a constant voltage of about 100 V to about 5,000 V or from about 500 V to about 2,000 V, or about 2000 V is applied to the separation channel 140 to drive electrophoretic migration of the charged analytes. Such constant voltage may be applied to drive electrophoretic migration of the charged analytes toward the junction of the TE reservoir in the sampling assembly 350 and the outlet of the separation channel 140.

With regard to varying with respect to time the pressure-driven counterflow of the fluid through the separation channel 140, such as, e.g., the LE fluid, such variation may be effective to control focusing of the charged analytes in the TE reservoir prior to introduction into the separation channel 140 and/or to control focusing of the charged analytes in the separation channel 140 prior to detection thereof. In this manner, charged analytes and TE fluid may be driven into an ionic interface, forming enriched ITP layers in the TE reservoir. Thus, controlled focusing of the charged analytes may be achieved outside of the separation channel 140 in the TE reservoir. In some embodiments, controlled focusing of the charged analytes may be achieved within the separation channel 140 prior to encountering the conductivity detection device 270 and/or the light source detection device 310 (i.e., upstream of the detection device 270 and/or the light source detection device 310).

In embodiments, controlled focusing of the charged analytes is achieved by ensuring that the current (which may serve a measure of occlusion of the separation channel 140) of fluid in the separation channel 140 does not exceed a threshold value. Thus, in embodiments, the current of fluid in the separation channel 140 is determined, detected, and/or monitored, such as, e.g., with a data acquisition device 320 communicatively coupled to the at least one separation channel and/or to the voltage supply device, to ensure that it does not exceed a threshold value. The threshold value for the current of fluid in the separation channel 140 may be from about 10 µA to about 500 µA. In embodiments wherein a single separation channel 140 is employed, the threshold value for the current of fluid in the separation channel 140 is from about 20 µA to about 30 µA. In one particular embodiment, the threshold value for the current of fluid in the separation channel 140 is about 23 µA. In embodiments wherein a bundle of separation channels 150 is employed, the threshold value for the current of fluid in the separation channel 140 is from about 310 µA to about 500 µA.

Generally, the pressure may be varied to ensure that the current of fluid in the separation channel 140 does not exceed the threshold value. In some embodiments, the pressure is varied when the current of the solution is determined to be about 90% of the threshold value. In embodiments, in view of the above-noted guidelines, the pressure is varied and/or adjusted to afford a constant current for focusing the charged analytes, such as, e.g., to afford a constant current that is about 80% of the threshold value. In some embodiments, the pressure is held at from about −700 Pa to about −200 Pa, or at from about −600 Pa to about −300 Pa, or at about −500 Pa. In general, however, the pressure is initially adjusted until a desired, constant current value is maintained. In this way, the TE fluid may be prevented from moving into the separation channel 140 and/or the prevented from encountering the detection device 270 and/or the light source detection device 310. Thus, the charged analytes may focus in between the LE solution and the TE solution in the TE reservoir and/or within a portion of the separation channel 140 upstream of the detection device 270 and/or the light source detection device 310. Such focusing of the charged analytes may be accomplished in from about 1 minute to about 10 minutes. Thus, the pressure may be varied: (i) to achieve controlled focusing of the charged analytes; (ii) to introduce the charged analytes into the separation channel 140 (and/or to a region thereof wherein the conductivity detection device 270 and/or the light source detection device 310 are located); and/or (iii) to deliver the charged analytes to a delivery reservoir.

With regard to introduction of the charged analytes into the separation channel 140 via the outlet thereof and/or migration of the charged analytes within the separation channel 140 to encounter the detection device 270 and/or the light source detection device 310, a pressure ramp is initiated. In general, the pressure may be adjusted such that it is decreased. More specifically, the pressure is generally adjusted, such as, e.g., decreased, to about −700 Pa to about −1,500 Pa, or to about −600 Pa to about −1,300 Pa, or to about −500 Pa to about −1,200 Pa. In particular embodiments, the pressure is adjusted at a rate of from about −10 Pa/s to about −25 Pa/s, or at a rate of about −20 Pa/s. Such may be completed in from about 125 to about 500 s. Generally, the pressure ramp may be terminated after the interface is detected via conductivity of the fluid in the separation channel 140 and/or the fluorescence emitted and/or excited by the charged analytes in the separation channel 140, as previously described and as described below. In embodiments, the pressure ramp is terminated once the interface of the charged analytes has passed and/or is downstream of the detection device 270 and/or the light source detection device 310. As shown in FIG. 17, once the current (µA) is low, such as, e.g., is reduced to approximately less than about 10 µA, the charged analytes have been incorporated into the separation channel 140 and/or have encountered the detection device 270 and/or the light source detection device 310. At this point, delivery of the charged analytes to a delivery reservoir may be initiated.

With regard to detecting separated, purified, concentrated, and/or quantified charged analytes in the sample via conductivity detection and/or fluorescence detection, in one or more embodiments, such is achieved via detecting and/or monitoring the conductivity of the fluid in the separation channel 140 and/or the fluorescence emitted and/or excited by the charged analytes in the separation channel 140 (wherein peaks may be determined). Such detection methods are known to those of ordinary skill in the art. In embodiments, the conductivity detection device 270 detects movement of the interface of the charged analytes (bracketed by the TE solution and the LE solution) thereby. After the conductivity detection device 270 detects movement of the interface thereby, the voltage is turned off and the pressure is adjusted to 0 Pa (thereby stopping flow of the solution in the separation channel 140). Similarly, in embodiments, the light source detection device 310 detects fluorescence of biomolecule sensor molecules, such as, e.g., DNA sensor molecules, in the LE fluid interacting with biomolecule analytes, such as, e.g., DNA. In some embodiments, the quantity of charged analytes in the sample may be determined via calculating the area under the curve provided via the fluorescence detection and comparing such calculation to a standard curve (such as is described in greater detail in the Example below).

With regard to delivery of the charged analytes to a delivery reservoir, in embodiments, the delivery of the charged analytes to the delivery reservoir includes: (1) placing a rinsing reagent, such as, e.g., TE fluid, in a rinsing reagent reservoir on the sampling platform 360 in contact with the outlet of the separation channel 140 via movement of the first and/or second moveable support structures 280, 300; (2) placing the outlet of the separation channel 140 within and/or above the delivery reservoir (which is a clean reservoir) via movement of the first and/or second moveable support structures 280, 300; and (3) extracting the charged analytes from the separation channel 140 into the delivery reservoir.

With regard to placing a rinsing reagent in contact with the outlet of the separation channel 140, in embodiments, the separation channel 140 is contacted with the rinsing reagent such that the rinsing reagent is not inserted within the separation channel 140. Such contacting is effective to remove environmental contaminants and/or biomolecule inhibitors from an outside surface of the separation channel 140. In embodiments, contacting the separation channel 140 with the rinsing reagent is performed in about 1 s.

With regard to placing the outlet of the separation channel 140 within and/or above the delivery reservoir, in embodiments, the delivery reservoir includes a delivery buffer, such as, e.g., Tris EDTA$^{-4}$. In further embodiments, the outlet of the separation channel 140 is contacted with the delivery buffer in the delivery reservoir. Such contact with the delivery buffer functions to aid in the extraction of the charged analytes from the separation channel 140. In alternative embodiments, the delivery reservoir does not include a delivery buffer and/or is empty prior to extraction of the charged analytes therein. Placing the outlet of the separation channel 140 within and/or above a delivery reservoir may be effected via movement in the X and/or Z (i.e., in the horizontal and/or vertical) direction of the first and/or second moveable support structures 280, 300.

With regard to extracting the charged analytes from the separation channel 140 into the delivery reservoir, in embodiments, varying the pressure of the headspace in the LE reservoir 160 achieves extraction of the charged analytes from the separation channel 140 into the delivery reservoir.

In embodiments, such variation of the pressure of the headspace to achieve extraction of the charged analytes involves adjusting, such as, e.g., increasing, the pressure to from about −1,500 Pa to about 2,000 Pa, or to from about −1,400 Pa to about 1,500 Pa, or to from about −1,200 Pa to about 1,000 Pa. In particular embodiments, the pressure is adjusted to about 2,000 Pa. Such delivery may be completed in from about 30 s to about 300 s. In this delivery step, the separation channel 140 and the electrophoretic assembly 110 may move in the X and/or Z (i.e., in the horizontal and/or vertical) direction via movement of the first and/or second moveable support structures 280, 300. In this way, the separation channel 140 and the electrophoretic assembly 110 may contact varying reservoirs, such as, e.g., rinsing reagent reservoirs and delivery reservoirs, in the sampling assembly 350.

In embodiments, the separation channel 140 is contacted with a storage reagent in a storage reagent reservoir on the sampling platform 36 following the delivery step. In embodiments, the storage reagent reservoir has a storage reagent, such as, e.g., distilled water, inserted therein. Such contact is effected via movement in the X and/or Z (i.e., in the horizontal and/or vertical) direction of the first and/or second moveable support structures 280, 300. In embodiments, the storage reagent is not inserted within the separation channel 140. In embodiments, the pressure is adjusted to about −700 Pa. In further embodiments, the separation channel 140 is contacted with the storage reagent in the storage reagent reservoir until an additional run of GEITP is performed and/or until the separation channel 140 is rinsed in between runs of GEITP. Such contacting may be effective to prevent evaporation of LE buffer and/or formation of crystals within the separation channel 140.

In embodiments wherein DNA is the charged analyte of interest, DNA may be detected separated, purified, concentrated, and/or quantified via GEITP as described herein in less than 5 minutes.

EXAMPLES

The following non-limiting examples illustrate use of an isotachophoretic apparatus.

Example 1: DNA Separation, Purification, Concentration, Quantification, and Delivery from a Crude Sample Using Gradient Elution Isotachophoresis 1. Materials and Methods
Buffer Solutions.
DNA purification, concentration, and delivery required several buffer solutions. LE solution had a measured pH of 8.2 and consisted of 50 mmol/L Tris (Sigma), 25 mmol/L HCl (Fluka), 0.1% w/w PVP (40 000 amu, Sigma), 0.1% w/w Triton-X 100 (Sigma), and 1×SYBR Green I (Molecular Probes). TE solution was 25 mmol/L Tris, 25 mM HEPES (Sigma), 0.1% w/w PVP, and 0.1% w/w Triton-X 100 with a measured pH of 8.0. Triton-X 100 was included in the LE and TE solutions, because this surfactant resulted in the degradation of cellular membranes during cell lysis of the buccal swab samples. PVP coated the capillary surfaces dynamically, with the intended purpose of aiding in eliminating the carry-over of DNA between samples. The fluorescent dye SYBR Green I allowed on-line DNA quantification using LIF during gradient elution isotachophoresis (i.e., GEITP). After purification and concentration, DNA molecules were delivered into a buffer solution that consisted of 10 mmol/L Tris and 0.1 mmol/L EDTA (Sigma).

Isotachophoretic Apparatus.

Figure 18:
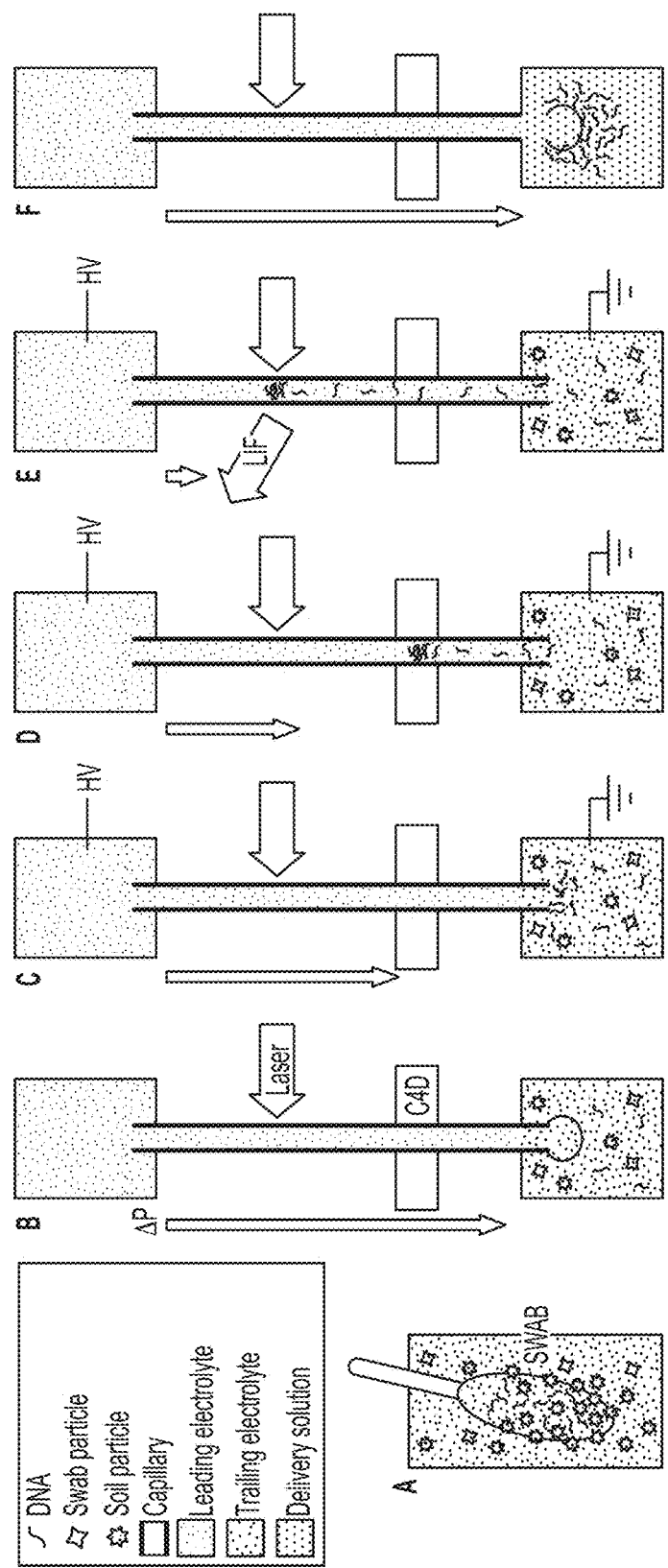
FIG. 18 is a schematic depicting DNA separation, purification, concentration, quantification, and delivery from a crude sample using a gradient elution isotachophoretic apparatus according to embodiments described herein, wherein: (A) human cells from a clean or soiled buccal swab were lysed; (B) the resulting sample in trailing electrolyte (i.e., TE) solution was transferred to a PCR tube and a controlled, variable pressure (indicated by vertical red arrow) allowed control over the location of the focusing interface between the leading electrolyte (i.e., LE) and TE solutions and prevented contaminants from entering the separation channel, (C) as the constant high voltage was applied and the pressure was reduced, DNA focused at the interface, (D) as the constant high voltage (indicated as HV) was applied and the pressure was reduced, DNA focused at the interface was transported past a C4D detector, (E) as the constant high voltage was applied and the pressure was reduced, DNA focused at the interface was transported past an LIF detector, and (F) the separated, purified, and concentrated DNA was extracted from the separation channel past the LIF detector for quantification and into a clean PCR tube for qPCR and STR analysis, as the voltage was removed and the pressure was increased.

A schematic of the experimental isotachophoretic apparatus is shown in FIG. 18. The upper end of a separation channel, i.e., a 9 cm long fused silica capillary with nominal outer and inner diameters of 360 and 75 μm, respectively, was affixed to the bottom of a polyetherimide reservoir containing 1 mL of LE solution using a miniature compression fitting from LabSmith (Livermore, Calif.) and Bondit B45TH epoxy from McMaster-Carr (Cleveland, Ohio). A custom autosampling stage controlled the placement of the lower end of the capillary into various solutions during analysis, as described below. The headspace pressure in the LE solution reservoir was regulated using a 20 mL, air-filled, disposable syringe driven by a custom syringe pump. Platinum electrodes were used to apply a high voltage of +2000 V dc from EMCO High Voltage (Sutter Creek, Calif.) at the LE solution reservoir and ground the solution electrically at the lower end of the capillary. The capillary passed through a custom LIF detector and a custom capacitively coupled contactless conductivity C4D detector from eDAQ Inc (Colorado Springs, Colo.). The laser-induced fluorescence (i.e., LIF) and conductivity detection points were approximately 58 and 44 mm from the lower end of the capillary, respectively. The apparatus was controlled and the data recorded using custom LabVIEW software from National Instruments (Austin, Tex.).

DNA Samples.

For method characterization, Plexor HY Promega Genomic DNA Standard (Madison, Wis.), comprised of a mixture of male individuals, was used as a control sample. The DNA concentration was determined to be 48.5±1.7 ng/μL (mean±SD) through qPCR using the Quantifiler Human Quantification Kit from Life Technologies (Grand Island, N.Y.). The control DNA solution was vortexed and diluted in TE solution to concentrations of 0.05, 0.17, 0.50, 1.5, and 5 ng/μL. The resulting samples were vortexed, and 100 μL of each were placed into 200 μL PCR tubes for analysis using the isotachophoretic apparatus.

To demonstrate the GEITP method for DNA purification, concentration, quantification, and delivery from crude samples for human identification, buccal swabs were collected from six anonymous human donors. A cotton-tipped swab containing a buccal sample was rehydrated with 120 μL of TE solution and placed into a 1.5 mL microcentrifuge tube containing 485 μL TE solution and 15 μL proteinase K solution (20 ng/μL) from Ambion® (Grand Island, N.Y.) for cell lysis. The cotton swab tip was submerged, and the swab stick was cut to allow the tube to close. The tube was then inverted by hand gently for approximately 30 s and placed into a hot water bath at 56° C. for 15 min for cell lysis. After vortexing briefly, fluid from the tube containing the swab was placed into 200 μL microcentrifuge tubes to create 1×, ⅓×, and ¹⁄₁₀× concentration samples with a final volume of 100 μL, diluted using TE solution. These samples were vortexed briefly just prior to analysis using the GEITP method.

Soiled buccal swabs were prepared to mimic crude environmental samples. Approximately 85-100 mg of soil collected for previous work was placed into 1.5 mL microcentrifuge tubes. A buccal swab containing a human buccal sample was rehydrated with 120 μL of TE solution and then placed into the tube containing soil, the stick was cut to allow the tube to close securely, and the tube was agitated by hand to coat the swab with soil thoroughly. The soiled swab was then prepared for analysis similarly to a clean swab. No attempt was made to avoid pipetting soil and other particulates into a 200 μL microcentrifuge tube for analysis using the GEITP method.

Quantitative PCR.

To determine the amount of DNA delivered from each sample, qPCR was performed using a 7500 Real-Time PCR System from Life Technologies (Grand Island, N.Y.) and Quantifiler Human DNA Quantification Kit from Life Technologies (Grand Island, N.Y.). The analysis used 8.2 μL Quantifiler Human Primer Mix, 9.8 μL Quantifiler Human PCR Reaction Mix, and 2 μL of the delivered DNA solution, for a total reaction volume of 20 μL. Amplification proceeded according to the manufacturer's recommended program of 95° C. for 10 min, followed by 40 cycles of 15 s at 95° C. and 1 min at 60° C. A standard curve was constructed for each plate using NIST Standard Reference Material 2372 Human DNA Quantitation Standard Component A at concentrations ranging from 52.44 to 0.07 ng/μL. An automatic threshold was applied to each plate using Applied Biosystems 7500 System SDS software version 1.2.3 (Grand Island, N.Y.). Each sample was measured in duplicate wells on the same plate.

STR Analysis.

STR analysis was performed to demonstrate human identification from DNA delivered from a crude sample using the GEITP method. STR analysis used the Promega PowerPlex 16 HS STR Amplification Kit. The 16 locus multiplex PCR kit contained primers to type the 13 core STR markers, the sex-typing marker Amelogenin, and the two additional STR markers Penta E and Penta D. The multiplex PCR reaction used a 12.5 μL total reaction volume containing 2.5 μL PowerPlex HS 5× Master Mix, 1.25 μL PowerPlex 16 HS Primer Set, 5 μL of the delivered DNA solution with a target DNA amount of 0.5 ng, and 3.75 μL deionized water. Thermal cycling was performed in a GeneAmp PCR System 9700 from Life Technologies (Grand Island, N.Y.) operating in the 9600 emulation mode with the following cycling parameters: 2 min incubation at 96° C.; 10 cycles of ramp 100% to 94° C. for 30 s, ramp 29% to 60° C. for 30 s, and ramp 23% to 70° C. for 45 s; 20 cycles of ramp 100% to 90° C. for 30 s, ramp 29% to 60° C. for 30 s, and ramp 23% to 70° C. for 45 s; and a 30 min incubation at 60° C. The temperature was subsequently held at 4° C. until the samples were removed.

Following multiplex PCR, 1 μL of amplified product was diluted in 10 μL Hi-Di formamide from Life Technologies (Grand Island, N.Y.) and 1 μL Internal Lane Standard 600 from Promega (Madison, Wis.) and analyzed with an ABI PRISM 3130 xl Genetic Analyzer using Data Collection v 3.0 software from Life Technologies (Grand Island, N.Y.), POP-4 polymer from Life Technologies (Grand Island, N.Y.), and a 36 cm capillary array. All genotyping was performed with GeneMapper ID v 3.2 software from Life Technologies (Grand Island, N.Y.) using allelic ladders, bins, and panels provided by the manufacturer and a peak detection threshold of 50 relative fluorescent units.

2. Experimental Protocol, Results, and Discussion

Figure 19:
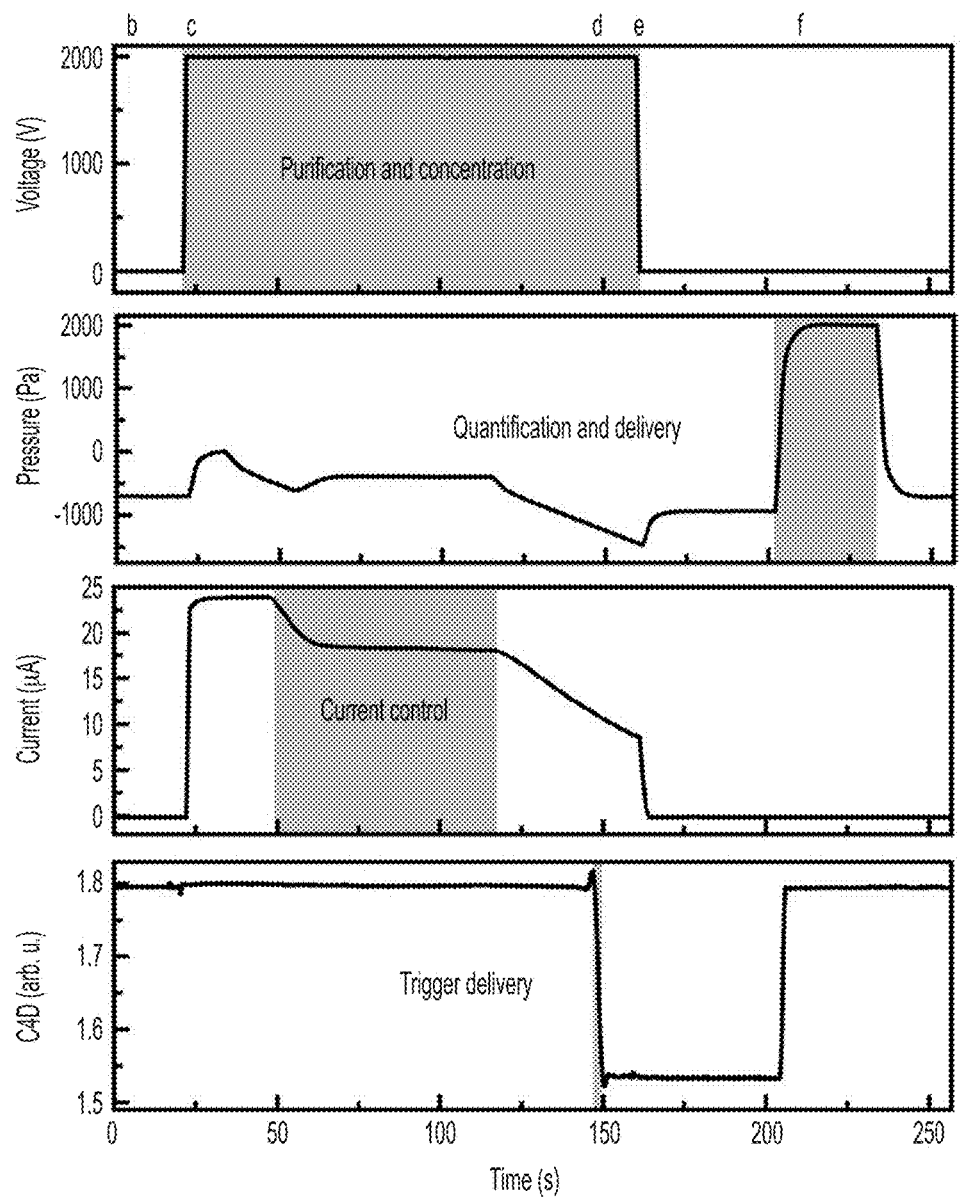
FIG. 19 depicts graphs of a procedure for DNA purification, concentration, and delivery from a crude sample using a gradient elution isotachophoretic apparatus according to embodiments described herein, wherein the: voltage, pressure, electrical current, and C4D detector signal are plotted versus time, wherein shaded areas highlight the times over which: the applied voltage induced DNA purification and concentration at the interface between the LE and TE solutions, the pressure was increased to drive DNA past the LIF detector for quantification and delivery, the electrical current was held constant to control the location of the focusing interface, and, the change in electrical conductivity between the LE and TE solutions as measured by the C4D detector triggered an automated DNA delivery sequence, and wherein the approximate times corresponding to the events shown are indicated as b-f, respectively.

The steps used for DNA purification, concentration, quantification, and delivery are shown schematically in FIG. 18, while the voltage, pressure, current, and C4D detector signal are plotted versus time in FIG. 19. Buccal swabs were first incubated in lysis buffer (see FIGS. 18(A) and 18), after which a portion of the sample was taken for analysis using the GEITP method. At the beginning of each analysis, the pressure applied to the LE solution reservoir was regulated at a value that ensured a slight flow of LE solution through the capillary to prevent TE solution or the crude sample from entering the lower end of the capillary. This pressure was slightly negative (−700 Pa) relative to the ambient pressure due to the height difference between the upper and lower ends of the capillary. The lower end of the capillary was then dipped into the sample in the TE solution reservoir, and 2 kV was applied (see FIG. 18(B)). At the same time, the pressure was increased to 0 Pa at the LE solution reservoir to prevent the ITP interface from migrating into the capillary. The pressure was then decreased at −20 Pa/s, and the focusing interface entered the capillary (see FIG. 18(C)). During this pressure ramp, the electrical current through the capillary was monitored. A typical current at the beginning of the analysis was approximately 23 µA. As the focusing interface entered the capillary, a decreasing current indicated that the capillary was filled partially with TE solution. The pressure ramp was stopped when the current reached approximately 18 µA, indicating that the focusing interface was inside the capillary near the capillary entrance. For the next 60 s, the pressure was adjusted to maintain a constant current. This held the interface at an approximately constant position to purify and concentrate DNA. The pressure was subsequently reduced at −20 Pa/s to transport the interface and the focused DNA past the C4D and LIF detectors (see FIGS. 18(D) and (E)). The interface was detected with the C4D detector, which triggered an automated DNA delivery sequence. Eight seconds after the interface passed the C4D detector, the high voltage was turned off and the applied pressure was set to −940 Pa, leaving the focused DNA stationary in the capillary. The lower end of the capillary was then rinsed in TE solution and placed into a clean 200 µL PCR tube containing 8.8 µL delivery solution. A pressure of 2 kPa was applied for 30 s to drive the purified and concentrated DNA past the LIF detector again for quantification and delivery into the clean tube (see FIG. 18(F)). The lower end of the capillary was then placed into 18M Ω cm water and the pressure at the LE reservoir returned to −700 Pa between analyses.

Figure 21A:
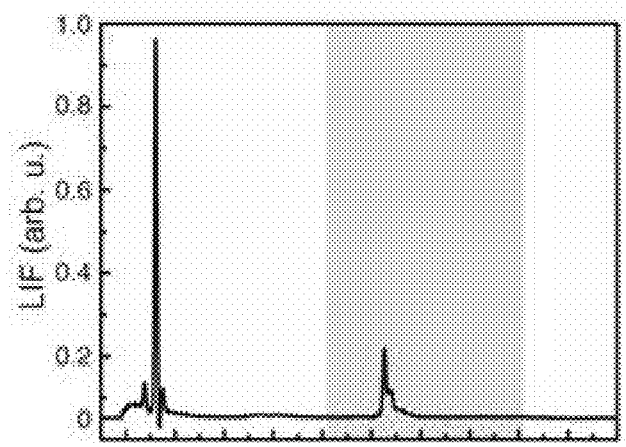
FIG. 21A depicts a graph of DNA quantification, wherein representative LIF signals for DNA delivered from a 0.5 ng/μL DNA control sample.
Figure 21B:
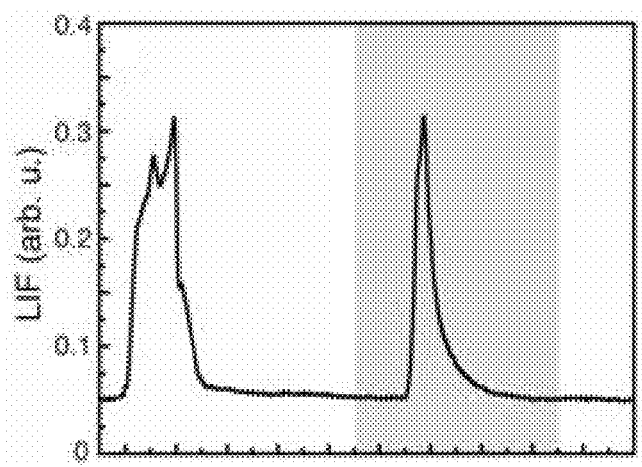
FIG. 21B depicts a graph of DNA quantification, wherein representative LIF signals for DNA delivered from a clean buccal swab sample.
Figure 21C:
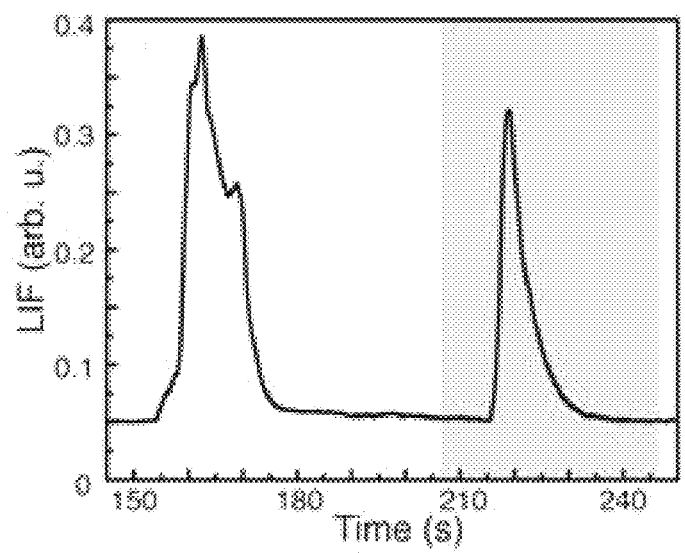
FIG. 21C depicts a graph of DNA quantification, wherein representative LIF signals for DNA delivered from a soiled buccal swab sample show comparable LIF signal quality, wherein shaded regions indicate the range of data used to determine the peak area for DNA quantification, wherein the apparent tailing of the second peak due to poiseuille flow after the voltage has been removed.
Figure 21D:
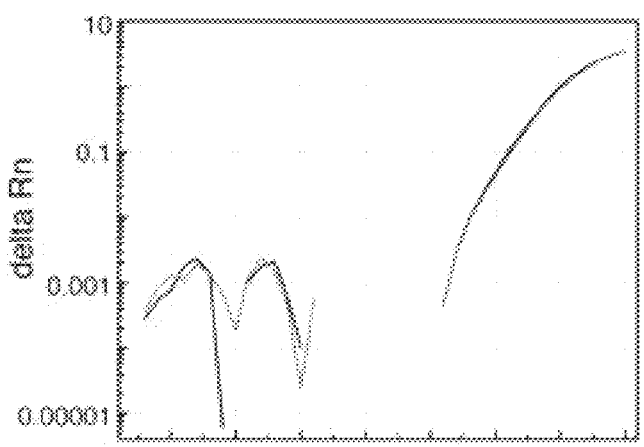
FIG. 21D depicts a graph of duplicate qPCR measurements of DNA delivered from a 0.5 ng/μL DNA control sample of FIG. 21A plotted as the fluorescence intensity of the amplified DNA relative to the intensity of an internal fluorescence standard, delta Rn, versus cycle number, with the average measured DNA concentrations noted, wherein threshold values are shown as dashed lines.
Figure 21E:
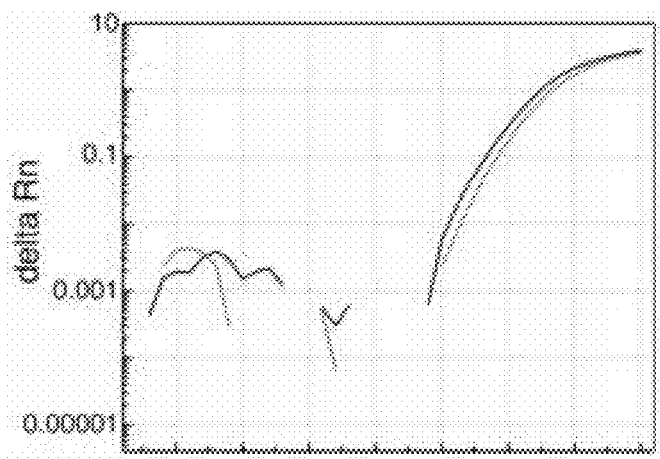
FIG. 21E depicts a graph of duplicate qPCR measurements of DNA delivered from the clean buccal swab of FIG. 21B plotted as the fluorescence intensity of the amplified DNA relative to the intensity of an internal fluorescence standard, delta Rn, versus cycle number, with the average measured DNA concentrations noted, wherein threshold values are shown as dashed lines.
Figure 21F:
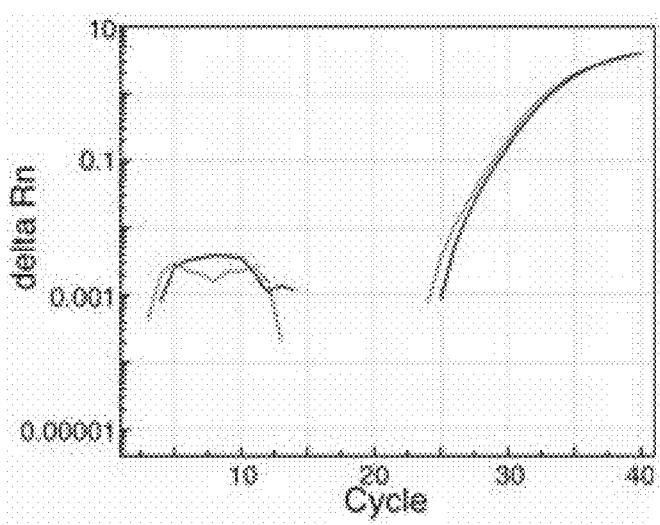
FIG. 21F depicts a graph of duplicate qPCR measurements of DNA delivered from the soiled buccal swab sample of FIG. 21C plotted as the fluorescence intensity of the amplified DNA relative to the intensity of an internal fluorescence standard, delta Rn, versus cycle number, with the average measured DNA concentrations noted, wherein threshold values are shown as dashed lines.
Figure 22:
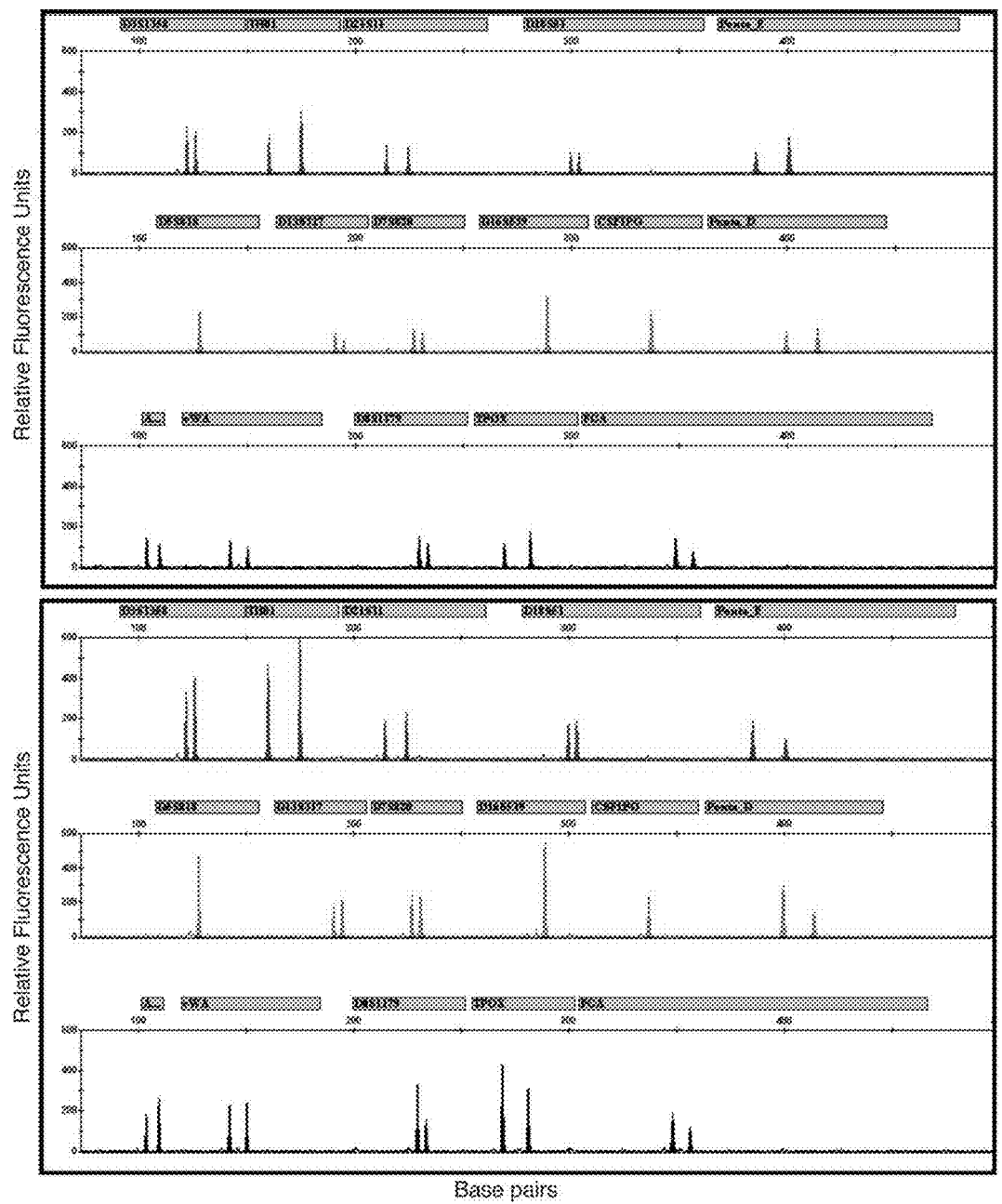
FIG. 22 depicts graphs of STR profiles from clean and soiled buccal swab samples. These representative full STR profiles were obtained from samples with 1× concentration from clean (top) and soiled (bottom) buccal swabs from the same individual and show comparable data that successfully locate all 16 STR loci, wherein each peak shows the presence of an allele for each STR locus, indicated using a gray box above the peaks.

The LIF signal was used for on-line DNA quantification during the delivery step. Representative fluorescence measurements for a 0.5 ng/µL control DNA sample, clean buccal swab, and soiled buccal swab show comparable performance between the samples (see FIGS. 21(A)-(C)). DNA passed the LIF detector twice during analysis, which resulted in two peaks. The earlier of these tended to have a variable shape, possibly due to the complex behavior of macromolecular polyelectrolytes focusing in the strong electric field gradient at the interface between the LE and TE solutions. Consequently, the later peak, which was measured after the electric field was removed and had a more regular shape, was used to quantify the amount of DNA delivered by calculating the area under the peak. This area was determined, with a baseline subtraction, using measurements from 11 s before (FIGS. 18(D) and 21(D)) to 29 s after triggering the delivery sequence. The baseline was calculated by a linear fit to the LIF signal for only the first and last 6 s of the data in this range.

Figure 20:
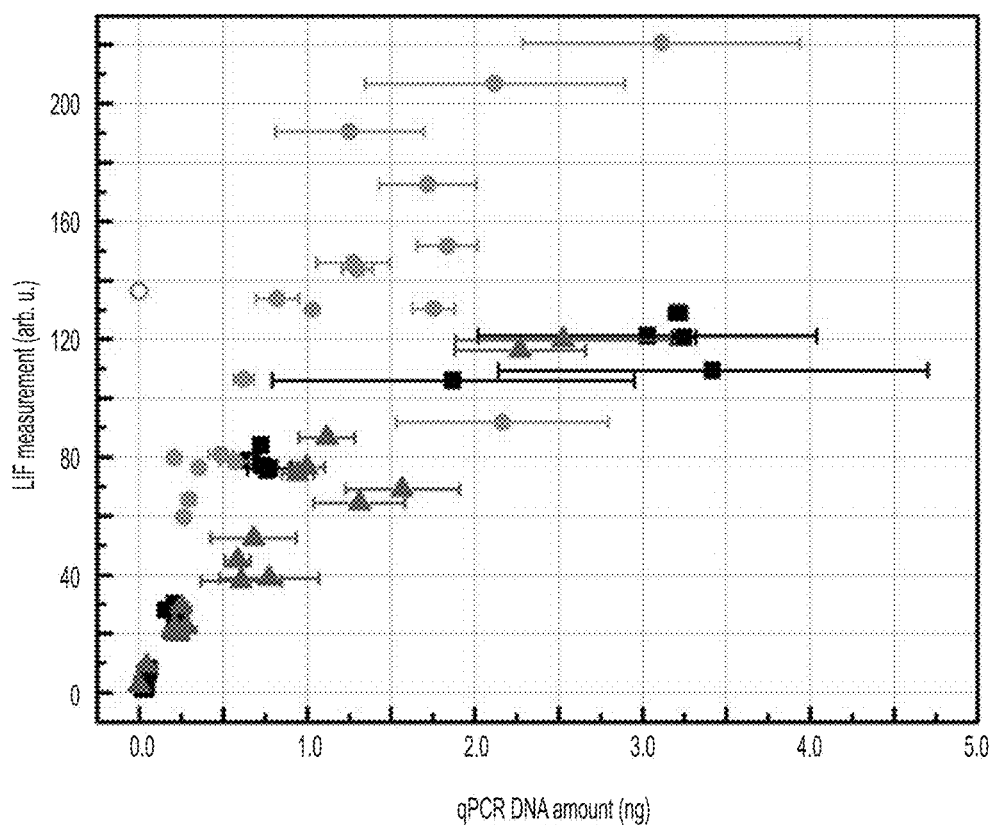
FIG. 20 is a graph of qPCR DNA amount (ng) with respect to LIF measurement (arb. u.) for DNA quantification, wherein: (1) results are shown for DNA extraction from DNA control samples (indicated by black squares), clean buccal swab samples (indicated by magenta triangles), and soiled buccal swab samples (indicated by green solid circles), (2) each data point represents measurements of DNA delivered from analysis using a gradient elution isotachophoretic apparatus according to embodiments described herein, with a single LIF measurement and qPCR results shown as the average and range of duplicate measurements, and (3) uncertainty in the y-axis due to error in the optical measurement was estimated to be smaller than the data point.

The LIF signal was calibrated against qPCR measurements to allow on-line DNA quantification in real time during analysis. Representative qPCR measurements of DNA delivered from a 0.5 ng/µL control DNA sample, clean buccal swab, and soiled buccal swab gave threshold cycles consistent with clean samples free of PCR inhibitors (see FIGS. 21(D)-(F)). As shown in FIG. 21, Referencing FIG. 20, the LIF measurements plotted versus the qPCR measurements are shown. Data for the control DNA samples and clean buccal swab samples show similar trends, indicating that the on-line LIF measurement can be used for DNA quantification for the clean buccal swab samples. However, LIF measurements for the soiled buccal swab samples were generally larger than expected from the trend measured with the control DNA samples. This is consistent with nonhuman DNA in the soil focusing along with human DNA in the sample and increasing the total amount of DNA measured using LIF. In contrast, the qPCR measurement used primers specific to human DNA only. To confirm this, the GEITP method was used to deliver DNA from a blank soiled swab sample with no human buccal cells. The result is plotted as the open circle in FIG. 20 and shows a significant amount of DNA measured using LIF, while the qPCR measurement detected no human DNA. As shown in FIG. 20, soiled buccal swab samples generally resulted in larger LIF measurements than clean buccal swab samples, for a given qPCR value, likely due to the presence of nonhuman DNA in the soil. Additionally, the green open circle in FIG. 20 represents a measurement of a blank soiled swab sample without human buccal cells. By calibrating the LIF measurements against qPCR measurements in this way, the amount of DNA delivered can be estimated during analysis in real time.

Reliable human identification using STR analysis requires that a specific amount of human DNA, between approximately 0.5 and 1.5 ng, be used for multiplex PCR. As implemented here, the GEITP method quantifies all DNA focused from the sample. For samples containing significant amounts of nonhuman DNA, the LIF measurement would ideally incorporate specificity for human DNA for subsequent human identification. The results in FIG. 20 indicate that the quantification provided by the on-line LIF measurement compares favorably with qPCR measurement and may be adequate, with specificity for human DNA, to eliminate the need for the additional quantification step prior to multiplex PCR.

DNA delivered using the GEITP method was suitable for human identification using STR analysis (see FIG. 21). Referencing FIG. 21, the average threshold cycles of 30.7, 29.8, and 30.2 for (D), (E), and (F), respectively, gave no evidence for significant inhibition due to contaminants present in the soiled buccal swab sample (see FIGS. 21(C) and (F)). Representative STR profiles from the same individual obtained from DNA delivered from clean and soiled buccal swab samples show comparable data that successfully locate all 16 STR loci. Clean and soiled buccal swab samples were also diluted in TE solution to ⅓× and ⅒× concentrations, and STR analysis was performed using the delivered DNA (see Table 1 below). GEITP delivered an appropriate amount of DNA for STR analysis for the undiluted samples, giving full STR profiles for all six clean and six soiled buccal swab samples. These clean and soiled buccal swab samples were in agreement for each individual, with average peak height ratios for heterozygous loci >80%. The fluorescence signal intensity was similar for these samples, with no DNA degradation apparent in the soiled buccal swab samples. However, diluting the DNA concentration in the sample prior to GEITP analysis resulted in a significant decrease in the amount of delivered DNA and, consequently, a loss of genetic information as STR profiles had an increasing number of alleles lost or loci dropped from the profiles. As implemented here, the GEITP method consistently delivered approximately 1% of the DNA in a sample, which is significantly less than the approximately 16-33% typical of more conventional techniques. Despite this drawback, the results shown here indicate that the GEITP method is adequate for DNA delivery from crude samples containing a relative abundance of DNA, as demonstrated using the soiled buccal swab samples. Further optimization of the GEITP method is expected to increase the efficiency of DNA purification and concentration for delivery.

TABLE 1

Reproducibility of STR analysis. DNA delivered using the GEITP method from clean and soiled buccal swab samples showed comparable results for human identification using STR analysis.

| Sample | Concentration | Loci identified[b] | Amount of DNA Delivered (ng)[c] | n |
|---|---|---|---|---|
| DNA control | 0.5 ng/μL | Mixture | 0.37 ± 0.08 | 2 |
| Blank swab | Negative control | 0 | —[d] | 1 |
| Blank soiled swab | Negative Control | 0 | —[d] | 1 |
| Clean buccal swab | 1[a] | 16 (16, 16) | 1.36 ± 0.58 | 6 |
|  | ⅓x[a] | 14 (11, 16) | 0.57 ± 0.24 | 6 |
|  | ¹⁄₁₀x[a] | 3 (0, 10) | 0.17 ± 0.07 | 6 |
| Soiled buccal swab | 1x[a] | 16 (16, 16) | 1.74 ± 0.53 | 6 |
|  | ⅓x[a] | 15 (8, 16) | 0.97 ± 0.34 | 6 |
|  | ¹⁄₁₀x[a] | 10 (4, 13) | 0.31 ± 0.11 | 6 |

[a]Concentration of the supernatant analyzed after cell lysis and diluted with TE solution.
[b]Reported as average (minimum, maximum) of 16 loci for n samples.
[c]Human DNA as measured by qPCR, (mean ± SD) of n samples.
[d]No human DNA detected.

The method presented here addresses several of the challenges associated with conventional techniques for DNA purification, concentration, and quantification from crude samples for human identification. First, GEITP requires no sample preparation, aside from suspension in a buffer solution for cell lysis; if this lysis solution also serves as the TE solution, DNA is purified and concentrated directly from the lysate. Additionally, no analysis steps are required to further purify or concentrate the DNA after delivery prior to STR analysis. Second, on-line DNA quantification can potentially eliminate the need for quantification by qPCR after DNA delivery. For samples containing significant amounts of nonhuman DNA, additional specificity for human DNA should be incorporated into the on-line quantitation. Third, nanogram amounts of DNA can be delivered into a small volume ≤10 μL, which is well matched to the volume requirements for input into the multiplex PCR reaction for STR analysis. Fourth, GEITP occurs in free solution, imposing no thresholds for low or high molecular weight DNA, as for gel-based methods, so that all of the DNA in the sample may be delivered. This capability is important for DNA delivery from aged or otherwise degraded samples. Finally, the GEITP method implemented here delivers DNA rapidly from crude samples in under 5 min after cell lysis, which is approximately 3-4 times faster than typical magnetic bead-based methods (Qiagen, EZ1R_DNA Investigator Handbook, 4th ed. 2009, www.qiagen.com/Knowledge-and-Support/Resource-Center/?catno=104640.) and an order of magnitude faster than the SCODA method. Because any DNA that may have carried over in the GEITP apparatus between deliveries was below the LOD, no additional time was required to change buffer solutions, rinse the capillary, or otherwise clean the apparatus between analyses.

The method described here based on GEITP enabled DNA purification, concentration, quantification, and delivery from crude samples with minimal sample preparation for human identification using STR analysis. In addition to the automated stand-alone format demonstrated here, GEITP is suitable for incorporation as a sample preparation step at the front end of a more complete DNA analysis system.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

It is noted that terms like "preferably," "generally," "commonly," and "typically" are not utilized herein to limit the scope of the claims or to imply that certain features are critical, essential, or even important to the structure or function of the claims. Rather, these terms are merely intended to highlight alternative or additional features that may or may not be utilized in a particular embodiment of the present disclosure.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

All documents cited are incorporated herein by reference; the citation of any document is not to be construed as an admission that it is prior art with respect to the present disclosure.

It is to be further understood that where descriptions of various embodiments use the term "comprising," and/or "including" those skilled in the art would understand that in some specific instances, an embodiment can be alternatively described using language "consisting essentially of" or "consisting of."

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless otherwise defined, all technical and scientific terms used herein have the same meaning as commonly understood by one of ordinary skill in the art to which the claimed subject matter belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

What is claimed is:

1. An apparatus for performing gradient elution isotachophoresis (GEITP) to separate charged analytes in a sample, the apparatus comprising:

a moveable electrophoretic assembly comprising:
  a separation unit,
  a detection unit operably connected to the separation unit, wherein the detection unit comprises:
    a detection unit support structure,
    a conductivity detection device accommodated by the detection unit support structure,
    a light source accommodated by the detection unit support structure, and
    a light source detection device accommodated by the detection unit support structure, and
  at least one moveable electrophoretic assembly support structure connected to at least one of the separation unit or the detection unit, wherein the at least one moveable electrophoretic assembly support structure is communicatively coupled to a motor, and wherein the at least one moveable electrophoretic assembly support structure and the motor are configured to provide movement of the moveable electrophoretic assembly in a Z direction or an X direction;
a sampling assembly operably connected to the moveable electrophoretic assembly; and
an apparatus support structure connected to at least one of the moveable electrophoretic assembly or the sampling assembly.

2. The apparatus of claim 1, wherein the separation unit comprises:
  at least one separation channel in a vertical orientation,
  a leading electrolyte (LE) reservoir in open fluidic communication with the at least one separation channel,
  a voltage supply device communicatively coupled to the at least one separation channel, and
  a pressure control device connected to the LE reservoir.

3. The apparatus of claim 2, wherein the separation unit includes a bundle of separation channels.

4. The apparatus of claim 1, wherein:
  the separation unit comprises at least one separation channel in a vertical orientation, and
  the detection unit support structure provides an interface for alignment of the conductivity detection device, the light source, the light source detection device, and the at least one separation channel, such that in operation:
    the conductivity detection device detects charged analytes present in the at least one separation channel,
    the light source directs light through the at least one separation channel, exciting and emitting fluorescence in charged analytes contacted with sensor molecules and present therein, wherein the sensor molecules are capable of fluorescing upon contact with the charged analytes, and
    the light source detection device detects the fluorescence emitted in the at least one separation channel.

5. The apparatus of claim 4, wherein the detection unit support structure:
  defines a separation channel cavity to accommodate the at least one separation channel therein,
  defines a light source cavity to accommodate the light source therein, wherein the light source cavity is provided at a fluorescence excitation angle, and
  defines a light source detection cavity to accommodate the light source detection device therein, wherein the light source detection cavity is provided at a fluorescence detection angle.

6. The apparatus of claim 5, wherein:
  the fluorescence excitation angle is from about 30° to about 150°, and
  the fluorescence detection angle is from about 30° to about 150°.

7. The apparatus of claim 6, wherein:
  the fluorescence excitation angle is formed by intersection of an axis of the light source and a plane bisecting the separation channel cavity and parallel to a first side surface of the detection unit support structure, and the fluorescence detection angle is formed by intersection of an axis of the light source detection device and a plane which bisects the separation channel cavity and is parallel to a second side surface of the detection unit support structure.

8. The apparatus of claim 1, wherein the at least one moveable electrophoretic assembly support structure comprises:
  a first moveable support structure communicatively coupled to a first motor, wherein the first moveable support structure and the first motor are configured to provide movement of the moveable electrophoretic assembly in a Z direction,
  a second moveable support structure communicatively coupled to a second motor, wherein the second moveable support structure and the second motor are configured to provide movement of the moveable electrophoretic assembly in an X direction, such that, in operation, the electrophoretic assembly is moveable in both the Z direction and the X direction.

9. The apparatus of claim 8, wherein the first moveable support structure is connected to the second moveable support structure.

10. The apparatus of claim 1, wherein the sampling assembly is moveable in a Y direction.

11. The apparatus of claim 1, wherein:
  the sampling assembly is connected to a sampling moveable support structure, and
  the sampling moveable support structure is communicatively coupled to a motor, wherein the sampling moveable support structure and the motor are configured to provide movement of the sampling assembly in a Y direction.

12. The apparatus of claim 1, wherein:
  the at least one moveable electrophoretic assembly support structure comprises:
    a first moveable support structure communicatively coupled to a first motor, wherein the first moveable support structure and the first motor are configured to provide translation of the moveable electrophoretic assembly in a Z direction, and
    a second moveable support structure communicatively coupled to a second motor, wherein the second moveable support structure and the second motor are configured to provide translation of the moveable electrophoretic assembly in an X direction, and
  the sampling assembly is connected to a third moveable support structure, wherein the third moveable support structure is communicatively coupled to a third motor, and wherein the third moveable support structure and the third motor are configured to provide translation of the sampling assembly in a Y direction.

13. The apparatus of claim 1, wherein:
  the separation unit comprises:
    at least one separation channel in a vertical orientation,
    a leading electrolyte (LE) reservoir in open fluidic communication with the at least one separation channel,
    a voltage supply device communicatively coupled to the at least one separation channel, and a pressure control device connected to the LE reservoir; and the sampling assembly comprises a trailing electrolyte (TE) reservoir and a delivery reservoir.

14. The apparatus of claim 13, wherein the TE reservoir comprises the sample and TE fluid, and wherein the apparatus further comprises a controller communicatively coupled to the moveable electrophoretic assembly and the sampling assembly, wherein the controller comprises a storage medium comprising computer readable and executable instructions and a processor for executing the computer readable and executable instructions wherein the processor executes the computer readable and executable instructions to:

(1) optionally pre-treat the at least one separation channel,
(2) insert LE fluid and sensor molecules capable of fluorescing upon contact with the charged analytes from the LE reservoir into the at least one separation channel,
(3) contact the at least one separation channel with the sample and TE fluid in the TE reservoir of the sampling assembly,
(4) separate the charged analytes via GEITP by:
  (a) producing a pressure-driven counterflow of the LE fluid through the at least one separation channel with the pressure control device and/or the voltage supply device,
  (b) applying a voltage to the at least one separation channel with the voltage supply device to produce an electric field, thereby driving electrophoretic migration of charged analytes in the TE reservoir of the sampling assembly toward the at least one separation channel, and
  (c) varying with respect to time the pressure-driven counterflow through the at least one separation channel with the pressure control device to control focusing of the charged analytes via initiation of a pressure ramp, thereby focusing and separating the charged analytes,
(5) direct light through the at least one separation channel to excite fluorescence in any of the charged analytes contacted with the sensor molecules,
(6) detect the charged analytes in the at least one separation channel via conductivity detection with the conductivity detection device and/or fluorescence detection with the light source detection device, and
(7) deliver the charged analytes to a delivery reservoir in the sampling assembly.

15. The apparatus of claim 14, wherein the LE fluid and the sensor molecules are inserted into the at least one separation channel in instruction (2) by increasing pressure in the LE reservoir with the pressure control device.

16. The apparatus of claim 14, wherein the at least one separation channel is contacted in instruction (3) with the sample and TE fluid in the TE reservoir of the sampling assembly by moving the moveable electrophoretic assembly in an X direction and/or a Z direction.

17. The apparatus of claim 14, wherein:
the voltage applied in instruction (4)(b) is a constant voltage of from about 100 V to about 5,000 V,
current in the at least one separation channel is monitored with a current detection device communicatively coupled to the at least one separation channel, and
the current is regulated with the pressure control device such that it does not exceed a threshold value.

18. The apparatus of claim 14, wherein the charged analytes are delivered to the delivery reservoir of the sampling assembly in instruction (7) by:
  (a) moving the moveable electrophoretic assembly in an X direction and/or a Z direction, and
  (b) increasing pressure in the LE reservoir with the pressure control device.

19. An apparatus for performing gradient elution isotachophoresis (GEITP) to separate charged analytes in a sample, the apparatus comprising:
a moveable electrophoretic assembly comprising:
  a separation unit,
  a detection unit operably connected to the separation unit, wherein the detection unit comprises:
    a detection unit support structure,
    a conductivity detection device accommodated by the detection unit support structure,
    a light source accommodated by the detection unit support structure, and
    a light source detection device accommodated by the detection unit support structure, and
  at least one moveable electrophoretic assembly support structure connected to at least one of the separation unit or the detection unit;
a sampling assembly operably connected to the moveable electrophoretic assembly, wherein the sampling assembly is connected to a sampling moveable support structure, wherein the sampling moveable support structure is communicatively coupled to a motor, and wherein the sampling moveable support structure and the motor are configured to provide movement of the sampling assembly in a Y direction; and
an apparatus support structure connected to at least one of the moveable electrophoretic assembly or the sampling assembly.

* * * * *